United States Patent
Karasawa et al.

(10) Patent No.: US 7,025,763 B2
(45) Date of Patent: Apr. 11, 2006

(54) MEDICAL APPARATUS

(75) Inventors: Hitoshi Karasawa, Hachioji (JP); Chie Yachi, Hachioji (JP)

(73) Assignee: Olympus Corporation, Tokyo (JP)

( * ) Notice: Subject to any disclaimer, the term of this patent is extended or adjusted under 35 U.S.C. 154(b) by 88 days.

(21) Appl. No.: 10/397,981

(22) Filed: Mar. 26, 2003

(65) Prior Publication Data
US 2003/0187429 A1 Oct. 2, 2003

(30) Foreign Application Priority Data

Mar. 26, 2002 (JP) ............................. 2002-086874
Mar. 26, 2002 (JP) ............................. 2002-086884
Dec. 25, 2002 (JP) ............................. 2002-374936

(51) Int. Cl.
*A61B 18/04* (2006.01)

(52) U.S. Cl. .......................................... 606/28; 606/29
(58) Field of Classification Search ............ 606/27–29, 606/51; 219/229; 30/140
See application file for complete search history.

(56) References Cited

U.S. PATENT DOCUMENTS

| | | | |
|---|---|---|---|
| 3,024,342 A * | 3/1962 | Birnbach et al. ............. | 30/140 |
| 3,117,578 A * | 1/1964 | Helbling ...................... | 606/28 |
| 4,206,759 A * | 6/1980 | Shaw .......................... | 606/28 |
| 4,662,068 A | 5/1987 | Polonsky | |
| 5,743,017 A * | 4/1998 | Dreher et al. ................ | 30/140 |
| 5,792,137 A | 8/1998 | Carr et al. | |
| 5,908,420 A * | 6/1999 | Parins et al. ................. | 606/51 |
| 6,060,695 A * | 5/2000 | Harle et al. ................. | 219/229 |
| 6,235,027 B1 | 5/2001 | Herzon | |
| 2004/0078035 A1* | 4/2004 | Kanehira et al. ............. | 606/28 |

FOREIGN PATENT DOCUMENTS

| | | |
|---|---|---|
| EP | 0 170 482 A2 | 2/1986 |
| JP | 2001-198137 | 7/2001 |
| JP | 2001-340349 | 12/2001 |
| WO | WO 01/12090 A1 | 2/2001 |

\* cited by examiner

*Primary Examiner*—Lee S. Cohen
(74) *Attorney, Agent, or Firm*—Scully, Scott, Murphy & Presser, P.C.

(57) ABSTRACT

The medical apparatus of this invention includes a therapeutic section at least having a blade for treating a living tissue thermally, a heat insulating part for insulating heat conduction from the blade to the main body of the medical apparatus. The therapeutic section and the heat insulating part are preferably provided on a grasping section (for example, a pair of jaws) for grasping the living tissue. It is preferable that the therapeutic section has a shape such that the living tissue and the side surface of the therapeutic section do not contact with each other. It is also preferable that the heat insulating portion has a shape such that the living tissue and the heat insulating portion do not contact with each other.

7 Claims, 13 Drawing Sheets

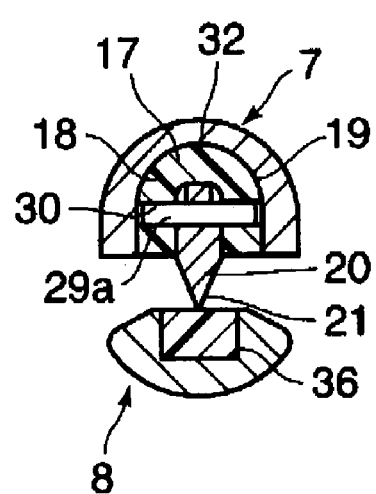
FIG. 3A
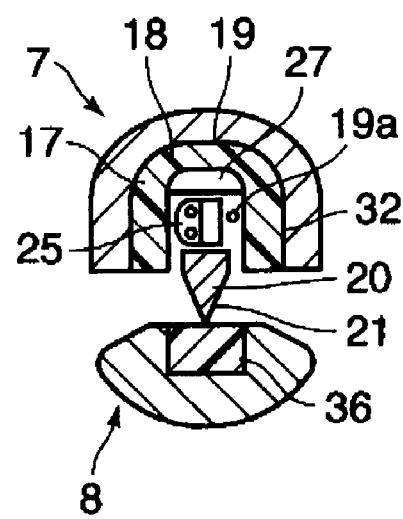
FIG. 3B
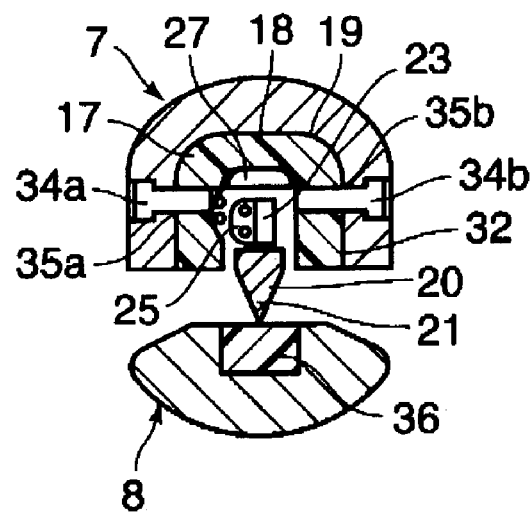
FIG. 3C
FIG. 4
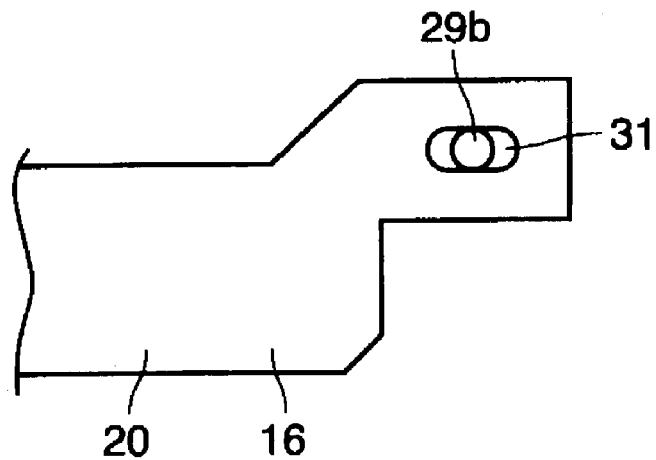

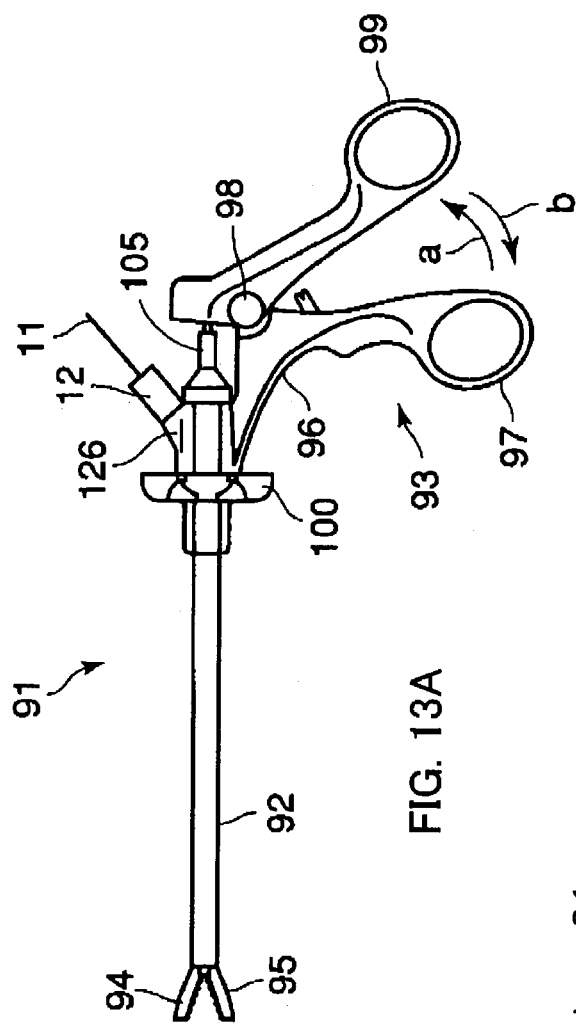
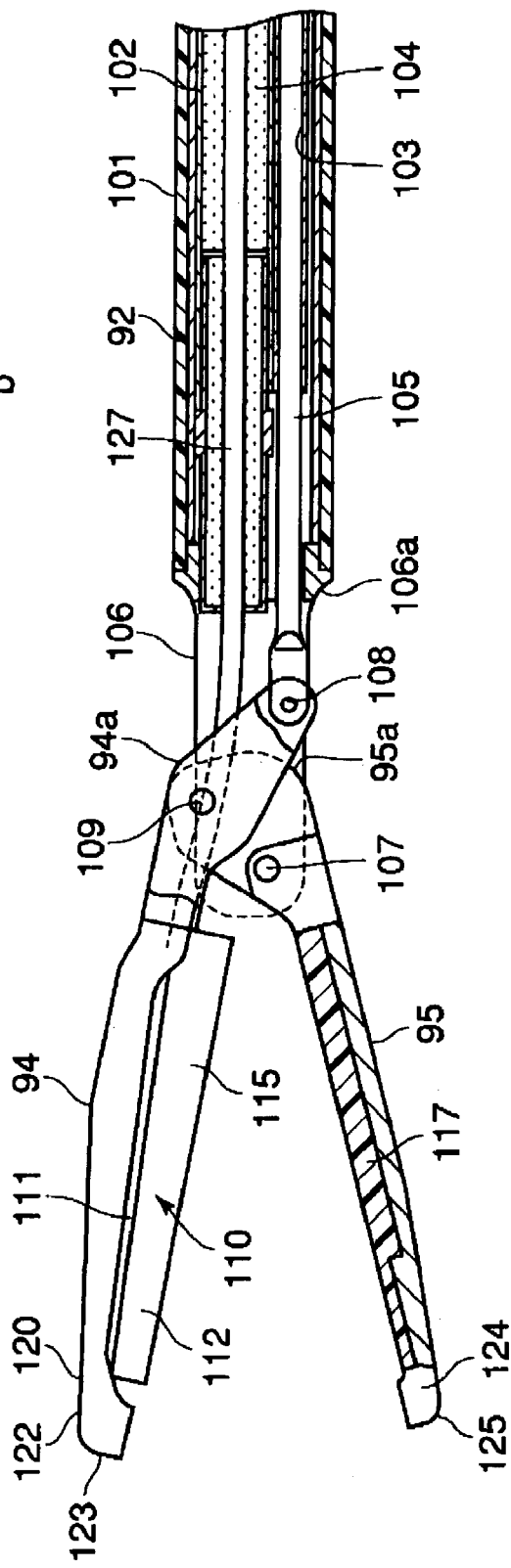
FIG. 13A
FIG. 13B

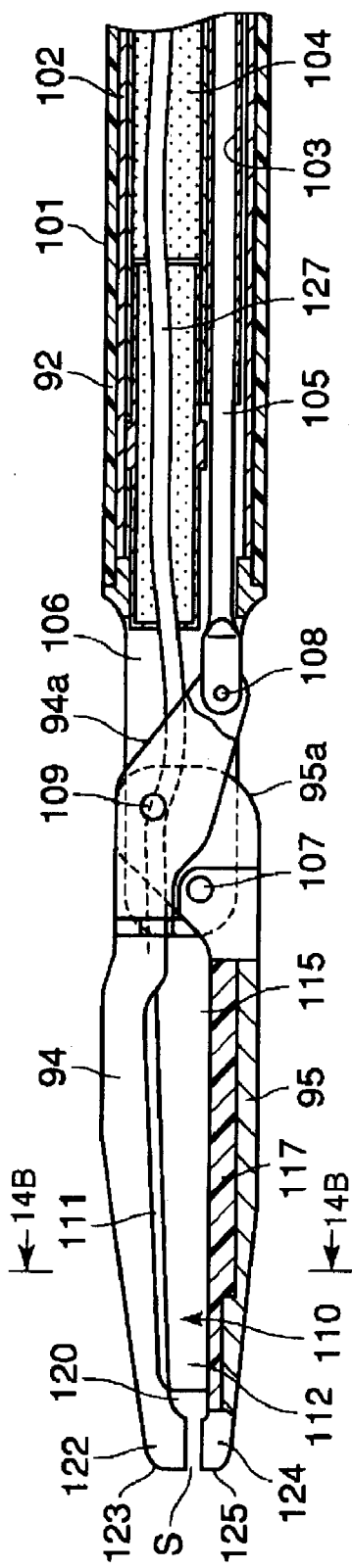
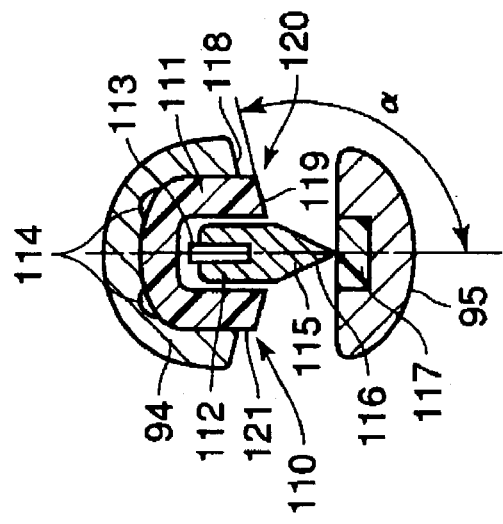
FIG. 14A
FIG. 14B

MEDICAL APPARATUS

CROSS-REFERENCE TO RELATED APPLICATIONS

This application is based upon and claims the benefit of priority from prior Japanese Patent Applications Nos. 2002-086874, filed Mar. 26, 2002, 2002-374936, filed Dec. 25, 2002, and 2002-086884, filed Mar. 26, 2002, the entire contents of each of the above applications are incorporated herein by reference.

BACKGROUND OF THE INVENTION

1. Field of the Invention

The invention relates to a medical apparatus constructed to heat a living tissue. The heating is often performed while the living tissue is grasped by a grasping section. This thermal treatment is performed for the purposes of, for example, coagulation of the living tissue or incision of a coagulated area.

2. Description of the Related Art

A medical apparatus is known that includes a pair of grasping sections for grasping a living tissue and a thermal element provided in either or both of the grasping sections, and which performs thermal treatment by heating the thermal element with a living tissue grasped. This thermal treatment is performed for the purposes of, for example, coagulation of the living tissue or incision of a coagulated area. This medical apparatus is generally used in various operation cases such as the arrest of bleeding at a blood vessel contained in a living tissue, the cauterization of an affected area or a bleeding area in a superficial part of a living tissue, and a blockage in a Fallopian tube for coagulation and contraception.

As this kind of medical apparatus, for example, JP-A-2001-198137 and JP-A-2001-340349 disclose constructions where at least one of a pair of grasping sections has a heat generating element such as a ceramic heater.

In each of these medical apparatus, a thermal plate (therapeutic part) for contact with a living tissue is provided in at least one of the grasping sections, and a heat generating element which is a heat source part is fixed to the thermal plate. Heat generated by the heat generating element is conducted to the thermal plate, and thermal treatment is performed to a living tissue by the thermal plate.

In the construction disclosed in JP-A-2001-340349, the cross-sectional shape of the thermal plate is such that the portion of the thermal plate that is in intimate contact with the heat generating element is smaller in width than the portion of the thermal plate that comes into contact with a living tissue. In this construction, heat generated at the heat generating element can be converged to effect efficiently coagulation and incision of a living tissue.

BRIEF SUMMARY OF THE INVENTION

A medical apparatus according to the invention includes: a therapeutic part having a blade for giving thermal treatment to a living tissue; and a heat insulating part made of a material lower in thermal conductivity than the therapeutic part, the heat insulating part being interposed between the other part of the medical apparatus and the blade.

In a preferable case, the medical apparatus further includes a grasping section for grasping a living tissue, and the therapeutic part with the thermal blade is provided on a living-tissue side of the grasping section. In this configuration, the heat insulating part may be provided between the grasping section and the blade.

The medical apparatus according to the invention proposes that thermal treatment to a living tissue is performed not by directly using a thermal element but by using the blade heated by the thermal element. The material of the blade is preferably a metal (for example, gold, silver, copper, copper alloy, aluminum alloy, tungsten or molybdenum). In many cases, as compared with thermal elements, blades have the advantages of large strength, large thermal capacity (the blades do not rapidly get cold) and freely formable shape. For this reason, in thermal treatment, it is preferable that thermal treatment be performed not by bringing the thermal element into direct contact with the living tissue, but by using the blade heated by heat generated by the thermal element and conducted to the blade.

Although there is a case where the therapeutic part is made of only a blade for thermal treatment, the therapeutic part may also include a member other than the blade for thermal treatment (for example, another blade not associated with thermal treatment).

On the other hand, since the blade has a large thermal capacity, a large amount of heat can be utilized for a thermal treatment of a living tissue by restraining thermal conduct from the blade to the grasping section and the main body of the medical apparatus. To fully utilize the large heat stored in the blade effectively, in the invention, a heat insulating part (for example, the material of the insulating part contains as its essential material fluororesin, silicone rubber, ceramics, glass, wood, pottery, asbestos, rubber or Teflon® and others) is interposed between the therapeutic part (a part having a blade for performing thermal treatment) and another member.

As described above, a major feature of the invention resides in the blade being used for thermal treatment to a living tissue and the heat insulating material for restraining heat conduction to another part of the medical apparatus to concentrate the heat in the blade to a thermal treatment.

Examples of a heat source part are a piece of nichrome wire, a silicon semiconductor and a molybdenum thin film resistor. The heat source part is preferably disposed in contact with the therapeutic part (particularly, the blade) because the efficiency of heat conduction is good.

Since the thermal element is, in many cases, smaller in size than the blade, it is preferable that the thermal element be not provided at the tip portion of the blade but be provided at the body portion of the blade so that heat is conducted to the tip portion from the thermal element on the body of the blade to heat the tip of the blade. In this case, the tip portion may be formed in a tapered shape to realize rapid heating.

It is also preferable that the shapes of the member (the blade, the insulating part or the grasping section) is constructed so that a living tissue in contact with the blade does not come into contact with the heat insulating part nor the grasping section. Such a portion in a member which prevents the living tissue from contacting to the heat insulating part or the grasping section can be called a contact preventing portion. For example, it is effective that the bottom end of the blade is positioned below the bottom end of the heat insulating part and the bottom end of the grasping section. In addition, it is also effective that the heat insulating part and the grasping section has outer side surfaces each having a chamfered portion at the bottom end.

It is preferable that the edge portion of the blade is covered with a non-tacky coat (for example, fluororesin) for preventing a living tissue or blood from sticking to the edge portion. Of course, it is far more preferable that the side surfaces of the blade be also covered with the coat.

The heat insulating part preferably has a shape with a concave portion that accommodates the heat source part and at least a part of the therapeutic part. This is because the effect of heat insulation is good. An example of this shape of the therapeutic part is a U-shaped cross-sectional shape.

In the medical apparatus, one of the suitable portions for thermal treatments is the grasping section (for example, jaws). In the case where the invention is to be applied to the grasping section, it is preferable that the blade be provided in one of a pair of grasping section and a blade receiving part (made of a material lower in thermal conductivity than the blade, for example, fluororesin or silicone) be provided in the other.

Since each constituent part expands thermally, parts are preferably assembled together with a margin for absorbing the difference in thermal expansion between the parts.

In addition, in the case where the therapeutic part (particularly, the blade), the heat insulating part and the heat source part are formed as one unit, assembly and disassembly becomes easy.

According to the invention, thermal treatment using the blade can be easily performed. Since the conduction of heat to the grasping section and the body is precluded by the heat insulating part, the invention is also advantageous in terms of the durability of the medical apparatus.

BRIEF DESCRIPTION OF THE SEVERAL VIEWS OF THE DRAWING

These and other features, aspects, and advantages of the apparatus and methods of the present invention will become better understood with regard to the following description, appended claims, and accompanying drawings where:

FIG. 3A is a cross-sectional view taken along line 3A-3A of FIG. 2A;

FIG. 3B is a cross-sectional view taken along line 3B-3B of FIG. 2A;

FIG. 3C is a cross-sectional view taken along line 3C-3C of FIG. 2A;

FIG. 4 is a side view showing the connection portion between a supporting pin of a holding frame of a heat insulating part and a thermal-expansion absorbing slot portion of a therapeutic part of the therapeutic instrument of the medical apparatus according to the first embodiment;

FIG. 13A is a side view showing a schematic construction of the entire therapeutic instrument of a medical apparatus according to a fifth embodiment of the invention;

FIG. 13B is a longitudinal sectional view of the essential parts of the therapeutic instrument, showing the state in which jaws are opened;

FIG. 14A is a longitudinal sectional view of the essential parts of a therapeutic instrument according to a fifth embodiment, showing the state in which jaws are closed;

FIG. 14B is cross-sectional view taken along line 14B—14B of FIG. 14A;

DETAILED DESCRIPTION OF THE INVENTION

Preferred embodiments of the present invention will be described hereinafter with reference to the drawings.

A first embodiment of the invention will be described below with reference to FIGS. 1 to 4.

Figure 1:
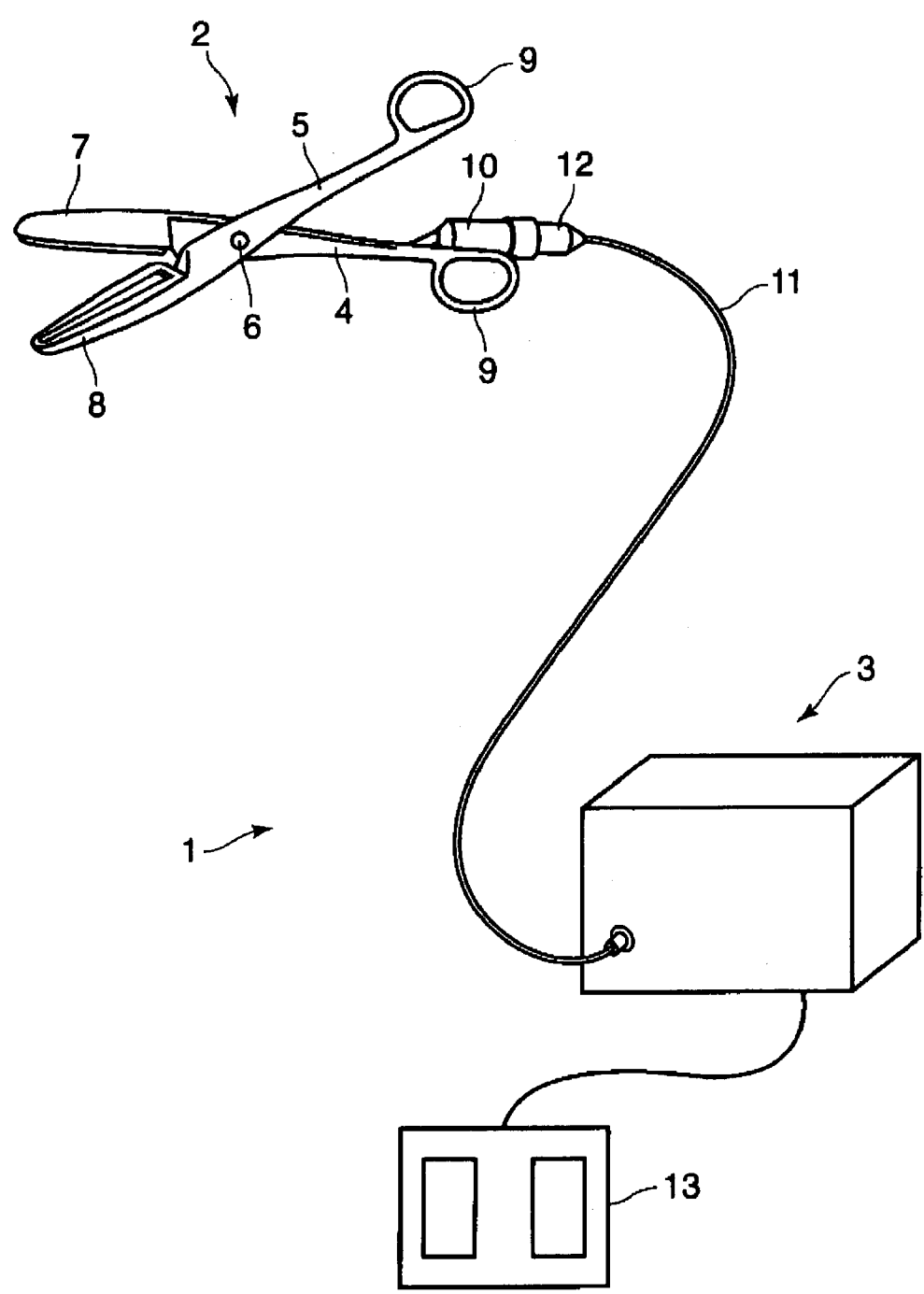
FIG. 1 is a schematic construction view of the entire system of a medical apparatus according to a first embodiment of the invention.

FIG. 1 shows a schematic construction of the entire system of a medical apparatus 1 according to the first embodiment. The system of this medical apparatus 1 includes a therapeutic instrument 2 and a power source 3.

The therapeutic instrument 2 includes two approximately straight' operating arms 4 and 5 (the first operating arm 4 and the second operating arm 5). These operating arms 4 and 5 are joined at their approximately central portions by a common rotating shaft 6 so that the operating arms 4 and 5 can be freely rotated about this rotating shaft 6.

Furthermore, a first grasping section 7 is formed in the first operating arm 4 on the distal tip side with respect to the rotating shaft 6, while a second grasping section 8 is formed in the second operating arm 5 on the distal tip side with respect to the rotating shaft 6. The first grasping section 7 and the second grasping section 8 can open and close about the rotating shaft 6, and thus forms a jaws section.

The rear ends of the first operating arm 4 and the second operating arm 5 respectively have rings (operating section) 9 through which an operator is to insert his/her finger and thumb to manipulate the first operating arm 4 and the second operating arm 5. The user operates the first operating arm 4 and the second operating arm 5 in the state of inserting his/her finger and thumb through the respective rings 9 of the first operating arm 4 and the second operating arm 5 to turn the first operating arm 4 and the second operating arm 5 about the rotating shaft 6, thereby opening and closing the first grasping section 7 and the second grasping section 8.

In addition, a connecting portion 10 is secured to the rear end of the first operating arm 4 in the vicinity of the ring 9 thereof. A connector 12 provided at one end of a cable 11 extending from the power source 3 is removably connected to the connecting portion 10.

A foot switch 13 for performing on/off switching of the power source 3 and adjustment of output setting of the power source 3 is connected to the power source 3.

Figure 2A:
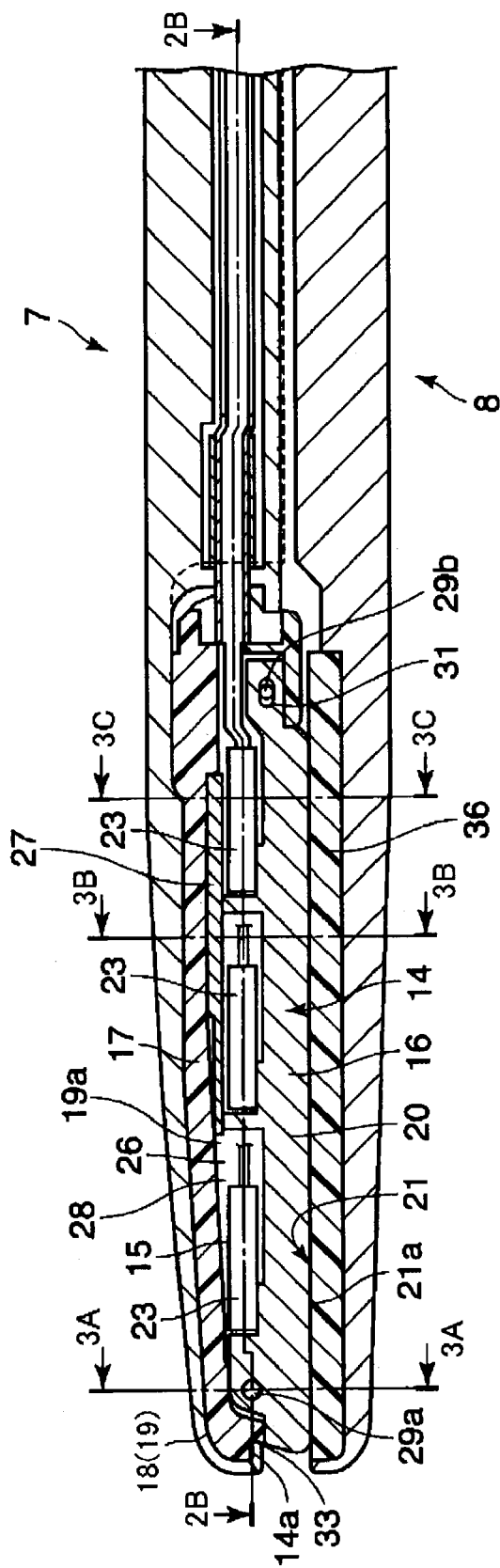
FIG. 2A is a longitudinal sectional view showing a tip portion of a therapeutic instrument of the medical apparatus according to the first embodiment.
Figure 2B:
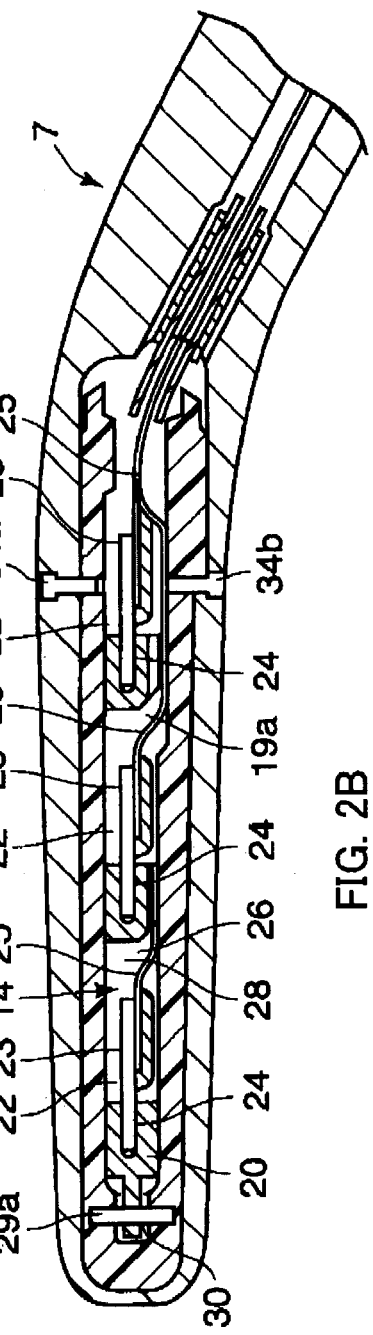
FIG. 2B is a cross-sectional view taken along line 2B-2B of FIG. 2A.

FIG. 2A is a cross-sectional view showing a distal tip portion of the therapeutic instrument 2. FIG. 2B is a cross-sectional view taken along line 2B—2B of FIG. 2A. FIG. 3A is a cross-sectional view taken along line 3A—3A of FIG. 2A.

FIG. 3B is a cross-sectional view taken along line 3B—3B of FIG. 2A. FIG. 3C is a cross-sectional view taken along line 3C—3C of FIG. 2A.

As shown in FIG. 2A, the first grasping section 7 is fitted with a thermal therapeutic unit 14 for performing thermal treatment to a living tissue. This thermal therapeutic unit 14 includes a heat source part 15 for generating heat used in thermal treatment to a living tissue, a therapeutic part 16 that is a blade that contains heat conducted from this heat source part 15 and performs thermal treatment to a living tissue, and a heat insulating part 17 which prevent, at least in part, the conduction of heat from the heat source part 15 toward portions other than the portion at which the heat source 15 contacts the therapeutic part 16. The heat insulating part 17 is disposed in the surrounding of the heat source part 15 and the therapeutic part (blade) 16.

The heat insulating part 17 has the function of holding the therapeutic part 16, and holds the therapeutic part 16 so that a blade edge part 21 (to be described later) that is formed in the therapeutic part 16 as a living tissue contact part for contact with a living tissue is exposed from the heat insulating part 17. The heat insulating part 17 is disposed in one of a pair of jaws of the jaws section in such a manner as to surround the heat source part 15. The heat insulating part 17 is made of a material which is lower in thermal conductivity than the therapeutic part (blade) 16.

The heat insulating part 17 includes a rigid, heat insulating frame 18 having an approximately U-like cross-sectional shape as shown in FIGS. 3A to 3C. This heat insulating frame 18 is made of a material which does not easily conduct heat, such as fluororesin, silicone rubber or ceramics. Other materials, such as glass, wood, pottery, asbestos, rubber and polytetrafluoroethylene (Teflon®) which are lower in thermal conductivity than the therapeutic part 16 and the grasping sections (jaws) 7 and 8 can also be used for the heat insulating frame 18. The heat insulating frame 18 has a function as a holding frame 19 which holds the therapeutic part (blade) 16.

In the first embodiment, the heat insulating frame 18 is adopted as the heat insulating part 17 and the heat insulating frame 18 is also used as the holding frame 19 which holds the therapeutic part 16. However, the holding frame 19 and the heat insulating frame 18 may be separately constructed, and the heat insulating frame 18 may be disposed on the outside of the holding frame 19 which accommodates the therapeutic part 16 and the heat source part 15 (i.e., on the side of the first grasping section 7), so that heat generated by the heat source part 15 cannot be easily conducted to any portion other than the therapeutic part 16.

Incidentally, the holding frame 19 that holds the therapeutic part (blade) 16 is preferably formed of a material having comparatively high rigidity so that the therapeutic part 16 is not bent or deformed even if strong forces are applied to the therapeutic part 16 from lateral directions. In addition, the holding frame 19 is preferably formed of a comparatively thick-walled rigid body so that the holding frame 19 can be given as high rigidity as possible.

The therapeutic part 16 is made of a material which is higher in thermal conductivity than the heat insulating part 17 which holds the therapeutic part 16, and is provided at a position to which heat is to be conducted from the heat source part 15, so that the therapeutic part 16 can give thermal treatment to the living tissue. Incidentally, the therapeutic part 16 is preferably fixed to the heat source part 15 so that heat can be conducted to the therapeutic part 16. This construction contributes to the promotion of the conduction of heat from the heat source part 15 to the therapeutic part 16.

The therapeutic part 16 also includes a heat conducting plate 20. As a part of the therapeutic part 16, the heat conducting plate 20 is made of a material which is higher in thermal conductivity than the heat insulating frame 18, such as gold, silver, copper, copper alloy, aluminum alloy, tungsten or molybdenum. The blade edge part 21 of tapered shape is formed at the bottom end of the heat conducting plate 20. At least an edge portion of the blade edge part 21 is covered with a thin coat 21a such as fluororesin in order to prevent a living tissue or blood from adhering to at least the edge portion.

As shown in FIG. 2B, at the top end of the heat conducting plate 20, mounting portions (concave portions) 22 for the heat source part 15 are formed in the portion of the heat conducting plate 20 that are accommodated into the holding frame 19. The heat source part 15 is provided with a plurality of (in the first embodiment, three) thermal elements 23 which are heat generating elements such as pieces of nichrome wire, silicon semiconductors, or molybdenum thin film resistors. Three heat source part mounting portions 22 which respectively accommodate the three thermal elements 23 are juxtaposed along the top end of the heat conducting plate 20.

In addition, fixing grooves 24 in which the respective thermal elements 23 are fixedly inserted at their tip portions are formed in separating walls which are respectively located immediately forwardly of the three heat source part mounting portions 22 at the top end of the heat conducting plate 20. The tip portions of the respective thermal elements 23 are fixed as by soldering in the state of being inserted in the fixing grooves 24 of the heat conducting plate 20.

One end of a lead 25 is fixed to the rear end portion of each of the thermal elements 23, such as by soldering. The lead 25 of each of the thermal elements 23 is extended toward the rear. The leads 25 of the respective thermal elements 23 are bundled at the rear end of the heat conducting plate 20, and extends further toward a user side and is connected to the connecting portion 10.

As shown in FIG. 2A, a groove-shaped accommodating space 19a which accommodates the upper portion of the heat conducting plate 20 which upper portion is extending upwardly from the blade edge part 21, the thermal elements 23 and the lead 25 is formed inside the holding frame 19. The upper portion of the heat conducting plate 20 extending upwardly from the blade edge part 21, the thermal elements 23 and the lead 25 are accommodated in the accommodating space 19a inside the holding frame 19, and are surrounded in a covered manner by the holding frame 19 (the heat insulating frame 18).

The accommodating space 19a inside the holding frame 19 has a large size to allow a gap 26 to be formed among the heat conducting plate 20, the thermal elements 23 and the lead 25. The gap 26 is filled with a spacer member 27 made of a hard plate difficult to bend, and a filler 28 having electrical insulating properties and heat insulating properties. In this manner, in the heat insulating part 17, the gap 26 between the holding frame 19 (the heat insulating frame 18) and the thermal elements 23 of the heat source part 15 is filled with the filler 28 having heat insulating properties.

As shown in FIG. 2A, the position of the distal tip of the holding frame 19 (the heat insulating frame 18) which covers the top portion of the heat conducting plate 20 is set to coincide with the position of the distal tip of the heat conducting plate 20, or to extend to a position protruding forwardly from the position of the distal tip of the heat conducting plate 20. Similarly, the position of the rear end of the holding frame 19 (the heat insulating frame 18) extends further rearwardly from the position of the rear end of the heat conducting plate 20 and covers the rear end of the heat conducting plate 20.

In addition, supporting pins 29a and 29b for the heat conducting plate 20 are respectively secured to the opposite front and rear ends of the holding frame 19. A first inserting hole 30 in which the supporting pin 29a disposed on the front side of the holding frame 19 is inserted is formed in the front end portion of the heat conducting plate 20. A second inserting hole 31 in which the supporting pin 29b disposed on the rear side of the holding frame 19 is inserted is formed in the rear end portion of the heat conducting plate 20. The heat conducting plate 20 and the holding frame 19 are supported in the state of being connected to each other by the front and rear supporting pins 29a and 29b.

As shown in FIG. 4, the second inserting hole 31 of the heat conducting plate 20 is formed by a slot which is long in the longitudinal direction of the heat conducting plate 20. The supporting pin 29b is loosely fitted for movement back and forth in the second inserting hole 31 in the longitudinal direction of the heat conducting plate 20. In addition, the second inserting hole 31 serves as a slot-shaped thermal expansion absorbing portion which absorbs the difference in thermal expansion between the heat conducting plate 20 and the holding frame 19.

As shown in FIGS. 3A to 3C, a concave fitting groove 32 in which the thermal therapeutic unit 14 is fitted is formed in the first grasping section 7. A stepped receiving portion 33 which locks into a front-end shoulder portion 14a of the thermal therapeutic unit 14 as shown in FIG. 2A is formed in the front end portion of the fitting groove 32. When the front-end shoulder portion 14a of the thermal therapeutic unit 14 is inserted into the receiving portion 33, the front-end shoulder portion 14a of the thermal therapeutic unit 14 disengageably locks into the front end portion of the first grasping section 7.

As shown in FIGS. 2B and 3C, the first grasping section 7 has two engagement pins 34a and 34b fitted in the rear end portion of the fitting groove 32. These engagement pins 34a and 34b are respectively press-fitted in pin inserting holes 35a and 35b formed in the rear end portion of the thermal therapeutic unit 14. Accordingly, when the thermal therapeutic unit 14 is in the state of being inserted in the fitting groove 32 of the first grasping section 7 and the front-end shoulder portion 14a of the thermal therapeutic unit 14 is in the state of being inserted in and locked to the stepped receiving portion 33 of the fitting groove 32, the thermal therapeutic unit 14 is fixed by the two engagement pins 34a and 34b press-fitted in the respective pin inserting holes 35a and 35b formed in the rear end portion of the thermal therapeutic unit 14.

As shown in FIGS. 3A to 3C, a plate-shaped receiving part 36 made of a flexible material which does not easily conduct heat, such as fluororesin or silicone, is provided on the surface of the second grasping section 8 that is opposite to the first grasping section 7. Accordingly, when the user closes the first grasping section 7 and the second grasping section 8, the whole of the blade edge part 21 of the heat conducting plate 20 is placed into contact with the receiving part 36. Then, the user clamps a living tissue between the first grasping section 7 and the second grasping section 8 with the first and second grasping sections 7 and 8 closed, and performs incision or coagulation on the living tissue.

The function of the above-described construction will be described below. During the use of the therapeutic instrument 2 according to the first embodiment, the user operates the first operating arm 4 and the second operating arm 5 of the therapeutic instrument 2 in the state of inserting his/her finger and thumb through the respective rings 9 provided on the user's sides of the first operating arm 4 and the second operating arm 5, thereby turning the first operating arm 4 and the second operating arm 5 with respect to each other about the rotating shaft 6. In this manner, the first grasping section 7 and the second grasping section 8 are opened and closed. Then, the user closes the first grasping section 7 and the second grasping section 8 to clamp a living tissue between the first grasping section 7 and the second grasping section 8, and energizes and heats the heat source part 15 of the thermal therapeutic unit 14.

At this time, heat from the three thermal elements 23 of the heat source part 15 is conducted to the heat conducting plate 20 and the tapered blade edge part 21 of the heat conducting plate 20 is heated to a high temperature. Accordingly, the living tissue pressed in contact with the blade edge part 21 of the heat conducting plate 20 between the first grasping section 7 and the second grasping section 8 is heated by the heat of the blade edge part 21, whereby the coagulation or the incision of the living tissue can be efficiently performed.

The first embodiment serves the following advantages. In the thermal therapeutic unit 14 of the therapeutic instrument 2 according to the first embodiment, the portion of the heat conducting plate 20 that extends upwardly from the blade edge part 21 and the thermal elements 23 are covered with the approximately U-shaped heat insulating frame 18. Accordingly, heat generated in the heat source part 15 (the thermal elements 23) is prevented from dissipating to other media and is concentratedly and efficiently conducted to the heat conducting plate (therapeutic section) 20 which is higher in thermal conductivity than the heat insulating frame (holding section) 18. In addition, owing to the heat insulating frame 18, the heat is not easily conducted to the first grasping section 7.

During the use of the medical apparatus 1, the heat of the thermal elements 23 can be prevented from dissipating in any direction other than the portion of contact between the thermal elements 23 and the heat conducting plate 20, for example, in rightward, leftward and upward directions from the heat conducting plate 20, whereby the heat of the thermal elements 23 as the heat generating elements of the heat source part 15 can be concentratedly and efficiently conducted to the heat conducting plate 20 of the therapeutic part 16. Accordingly, the heat of the heat source part 15 can be prevented from being conducted to the first grasping section 7. Consequently, it is possible to prevent the degradation of the coagulation performance and the incision performance of the medical apparatus 1 due to the temperature of the heat conducting plate 20 in contact with a living tissue not increasing rapidly or a temperature nonuniformity occurring.

In addition, in the first embodiment, the three heat source part mounting portions 22 having concave shapes are juxtaposed along the top end of the heat conducting plate 20, and the three thermal elements 23 are respectively accommodated in the heat source part mounting portions 22. The respective tip portions of the three thermal elements 23 are fixed as by soldering in the state of being inserted in the fixing grooves 24 which are respectively formed in the separating walls located forwardly of the heat source part mounting portions 22. In addition, the portion of the heat conducting plate 20 extending upwardly from the blade edge part 21, the thermal elements 23 and the lead 25 are accommodated in the accommodating space 19a inside the holding frame 19, and the holding frame 19 (the heat insulating frame 18) is disposed to surround the portion of the heat conducting plate 20 extending upwardly from the blade edge part 21, the thermal elements 23 and the lead 25. The holding frame 19 (the heat insulating frame 18) which holds the therapeutic part 16 is made of a material having comparatively high rigidity, and has a wall thickness having predetermined rigidity. Furthermore, the gap 26 is large which is formed among the heat conducting plate 20 and the thermal elements 23 such as the heat generating elements of the heat source part 15 inside the holding frame 19 is large. Consequently, even if a strong force is applied to the first grasping section 7 or the heat conducting plate 20 from a lateral direction, the force can be reduced by the filler 28 provided in the gap 26. Consequently, even in the case where the thermal elements 23 repeat heating, the securing of the thermal elements 23 as the heat generating elements of the heat source part 15 to the first grasping section 7 can be prevented from becoming imperfect, the deformation of the heat conducting plate 20 can be prevented, and the thermal elements 23 themselves can be prevented from being damaged by stress from the first grasping section 7.

Furthermore, the second inserting hole 31 of the heat conducting plate 20 is formed by a slot which is long in the longitudinal direction of the heat conducting plate 20, and the supporting pin 29b of the holding frame 19 is loosely fitted for movement back and forth in the second inserting hole 31 in the longitudinal direction of the heat conducting plate 20. Consequently, even in the case where the temperature of the heat generating elements serving as the thermal elements 23 greatly varies between their in-use state (high temperature) and their not-in-use state (normal temperature), it is possible to absorb the deviation of the position of the hole for the supporting pin 29b due to the difference in extension in the longitudinal direction between the heat conducting plate 20 and the holding frame 19. Consequently, during heating by the thermal elements 23, the difference in thermal expansion in the longitudinal direction between the heat conducting plate 20 and the holding frame 19 can be absorbed by the portion of engagement between the slot of the second inserting hole 31 and the supporting pin 29b of the holding frame 19. Consequently, the thermal elements 23 can be safely and reliably fixed so that such stress that causes damage to the heat generating elements is not applied to the thermal elements 23.

A second embodiment of the invention will be described below with reference to FIGS. 5A to 5C. In the second embodiment, the construction of the therapeutic instrument 2 of the medical apparatus 1 according to the first embodiment (refer to FIGS. 1 to 4) is modified as will be described below. Incidentally, the second embodiment is approximately the same as the first embodiment in the basic construction of the therapeutic instrument 2, and in the description of the second embodiment, the same reference numerals are used to denote the same sections, parts and portions as those of the first embodiment and the same description is omitted.

Figure 5A:
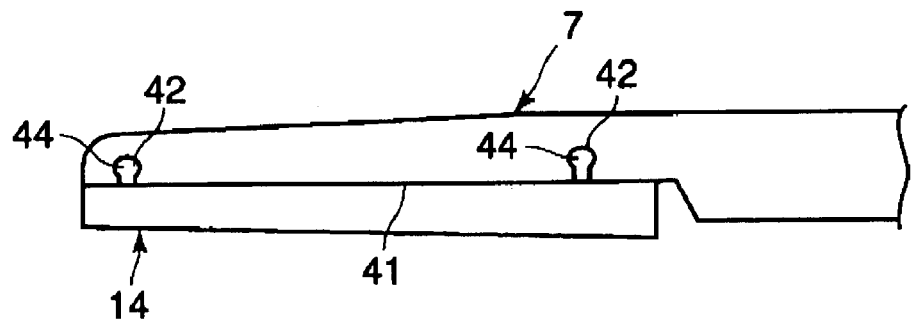
FIG. 5A is a side view showing the essential parts of the connection portion between a jaw and a therapeutic part of a therapeutic instrument of a medical apparatus according to a second embodiment of the invention.

Namely, as shown in FIG. 5A, in the therapeutic instrument 2 of the second embodiment, the first grasping section 7 is provided with a planar, unit securing surface 41, and the thermal therapeutic unit 14 is removably secured to the unit securing surface 41. A plurality of engaging holes 42 are formed on the unit securing surface 41 of the first grasping section 7.

Figure 5B:
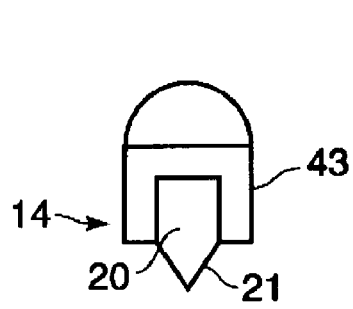
FIG. 5B is a front view of the essential parts shown in FIG. 5B.

As shown in FIG. 5B, the thermal therapeutic unit 14 includes a rigid, heat insulating frame 43 having an approximately U-like shape in cross section.

Figure 5C:
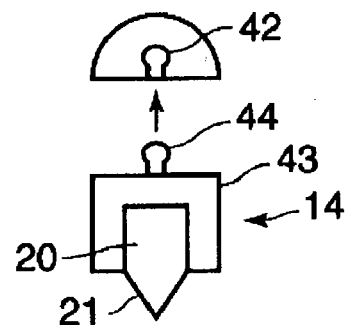
FIG. 5C is a front view showing the state in which the connection portion between the jaw and the therapeutic part is disengaged.

As shown in FIG. 5C, a plurality of engaging convex portions 44 which detachably engage with the respective engaging holes 42 of the first grasping section 7 are disposed to protrude from the top surface of the heat insulating frame 43.

The second embodiment can serve the following advantages. Namely, in the therapeutic instrument 2 of the second embodiment, the approximately U-like shaped heat insulating frame 43 covers the portion of the heat conducting plate 20 that extends upwardly from the blade edge part 21, and the thermal elements 23 (refer to FIGS. 2A and 2B). Accordingly, heat generated in the heat source part 15 (the thermal elements 23) can be concentratedly and efficiently conducted to the heat conducting plate (therapeutic section) 20 which is higher in thermal conductivity than the heat insulating frame (holding section) 43, but can be prevented from being easily conducted to the jaws side. During the use of the medical apparatus 1, the heat of the thermal elements 23 can be prevented from escaping in any direction other than the portion of contact between the thermal elements 23 and the heat conducting plate 20, for example, in rightward, leftward and upward directions from the heat conducting plate 20, whereby the heat of the thermal elements 23 such as the heat generating elements of the heat source part 15 can be concentratedly and efficiently conducted to the heat conducting plate 20 of the therapeutic part 16. Consequently, even in the second embodiment, similarly to the case of the first embodiment, the heat of the heat source part 15 can be prevented from being conducted to the first grasping section 7. Consequently, it is possible to prevent the degradation of the coagulation performance and the incision performance of the medical apparatus 1 due to the temperature of the heat conducting plate 20 in contact with a living tissue not increasing rapidly or a temperature nonuniformity occurring.

Figure 6:
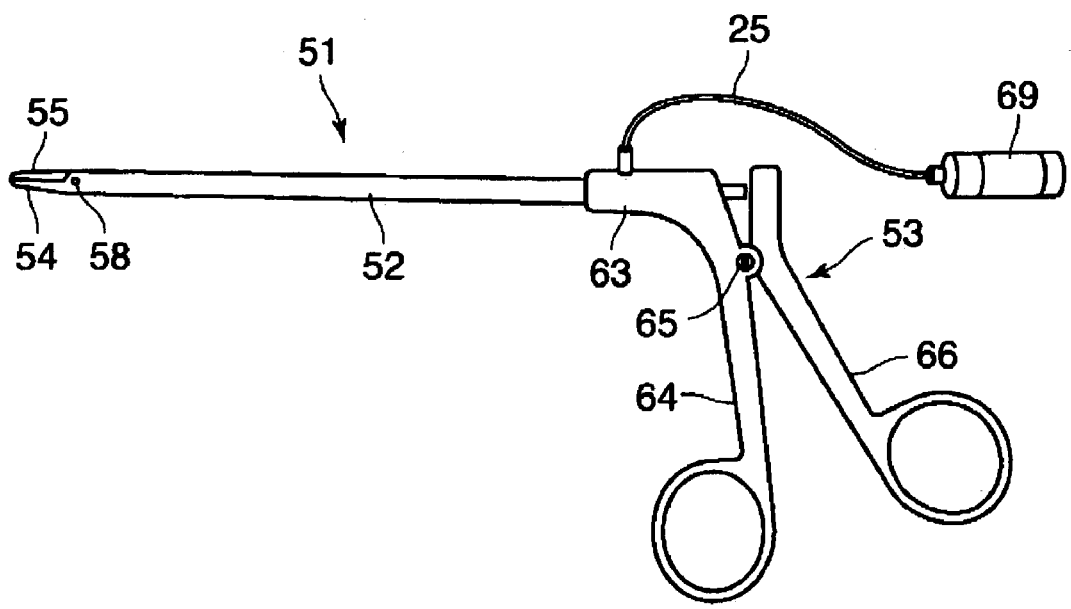
FIG. 6 is a side view showing a therapeutic part of a therapeutic instrument of a medical apparatus according to a third embodiment of the invention.

A third embodiment of the invention will be described below with reference to FIGS. 6 to 8B. FIG. 6 shows thermal coagulation incising forceps 51 for endoscopic operation as a medical apparatus according to the third embodiment. The thermal coagulation incising forceps 51 of the third embodiment include an elongated inserting section 52 and a user-side operating section 53 which is connected to the proximal side of this inserting section 52.

Figure 7A:
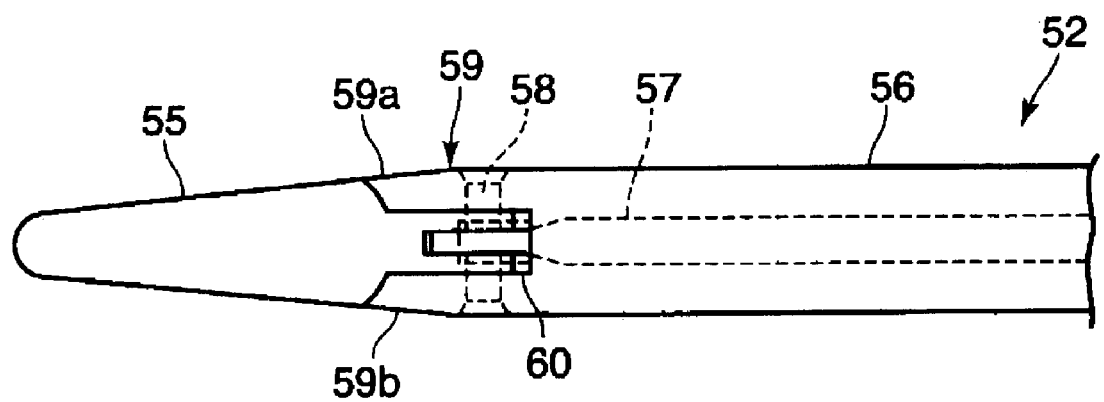
FIG. 7A is a plan view showing a distal tip portion of the therapeutic part of the third embodiment.
Figure 7B:
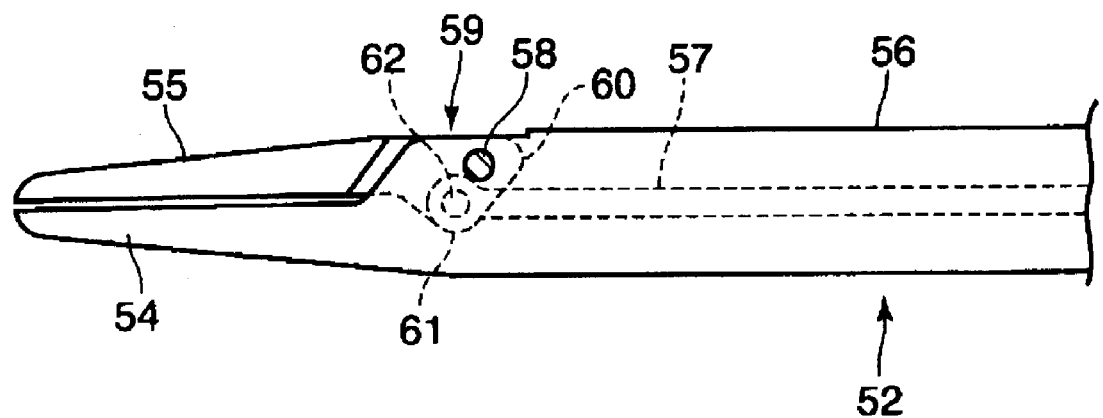
FIG. 7B is a side view of the same distal tip portion.

The inserting section 52 has a stationary jaw 54 and a movable jaw 55 at its distal tip portion. As shown in FIGS. 7A and 7B, the inserting section 52 includes an outer pipe 56 and a driving shaft 57 that is axially movably inserted through the interior of the outer pipe 56. The stationary jaw 54 is formed integrally with the distal tip portion of the outer pipe 56 of the inserting section 52.

The proximal end of the movable jaw 55 is supported at the distal tip of the outer pipe 56 for rotation about a rotating shaft 58 disposed in a direction perpendicular to the axial direction of the outer pipe 56. As shown in FIG. 7A, an approximately U-like shaped axial supporting portion 59 is formed at the distal tip of the outer pipe 56. Two axial supporting arms 59a and 59b are disposed in parallel with each other in the axial supporting portion 59. A rotating shaft 58 is disposed to pass between these axial supporting arms 59a and 59b.

Furthermore, an elongated extending portion 60 is formed at the proximal end of the movable jaw 55 in such a manner as to be inserted between the two axial supporting arms 59a and 59b. As shown in FIG. 7B, the extending portion 60 has a hill-shaped protruding portion 61 protruded downwardly from the rotating shaft 58. The distal tip of the driving shaft 57 is connected to the protruding portion 61 for turning movement about a pivot shaft 62.

As shown in FIG. 6, the operating section 53 includes a operating-section main body 63, a stationary handle 64 provided integrally with the operating-section main body 63, and a movable handle 66 provided on the operating-section main body 63 for turning movement about a pivot shaft 65. In addition, the user-side tip of the driving shaft 57 is connected to a top end portion of the movable handle 66.

As the movable handle 66 is manipulated to turn about the pivot shaft 65 with respect to the stationary handle 64, the driving shaft 57 is driven to move back and forth in the axial direction. As the driving shaft 57 is moved back and forth, the movable jaw 55 is driven to rotate about the rotating shaft 58 with respect to the stationary jaw 54, whereby the stationary jaw 54 and the movable jaw 55 are operated to open and close.

Figure 8A:
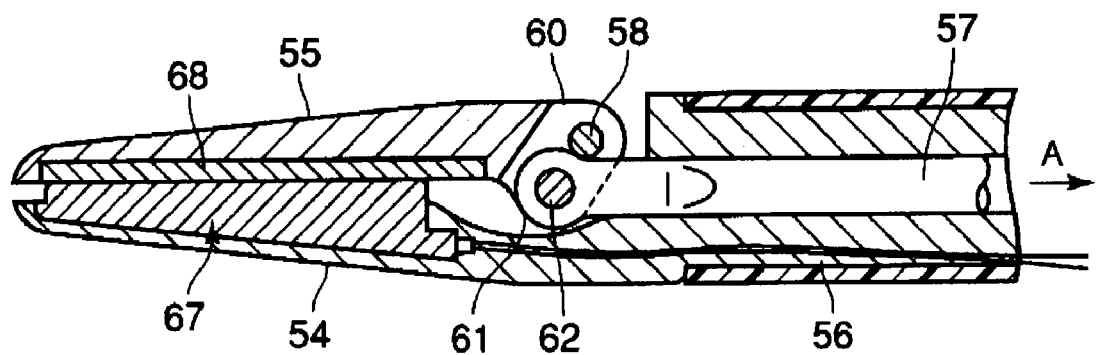
FIG. 8A is a longitudinal sectional view of the essential portions of the therapeutic part of the third embodiment, showing the state in which jaws are closed by the function of the therapeutic part.
Figure 8B:
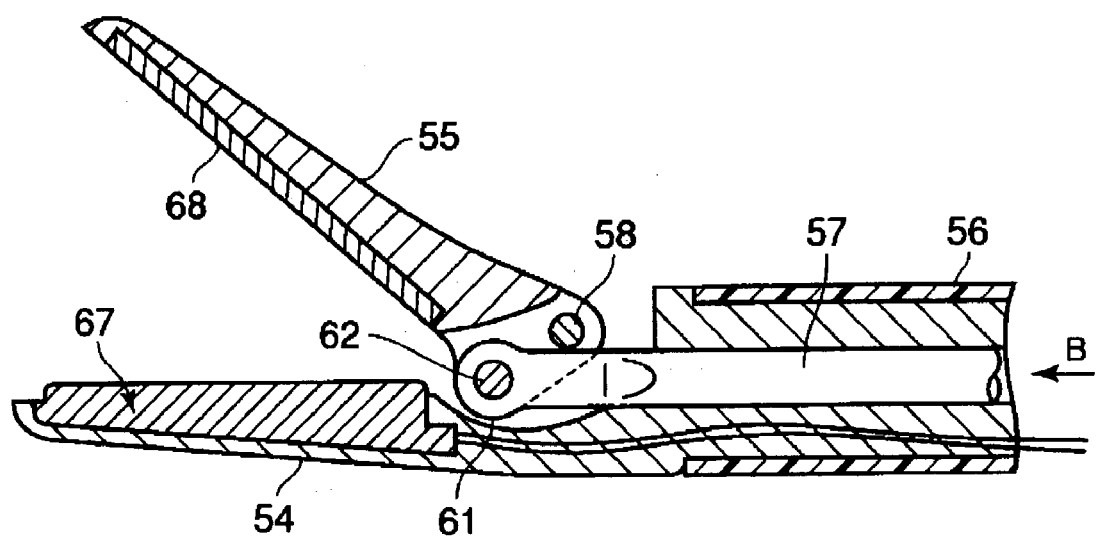
FIG. 8B is a longitudinal sectional view of the essential portions of the therapeutic part of the third embodiment, showing the state in which the jaws are opened by the function of the therapeutic part.
Figure 9:
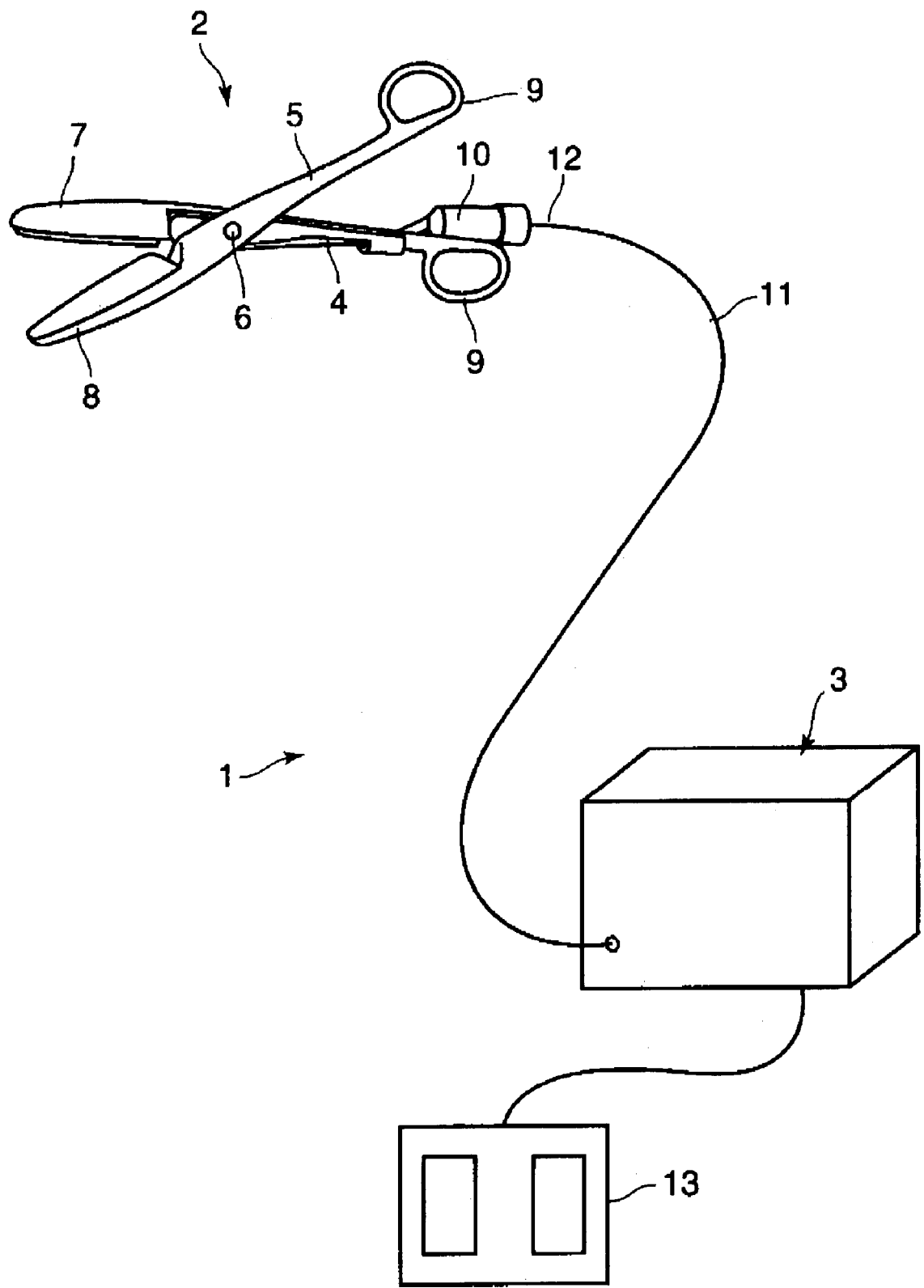
FIG. 9 is a schematic construction view of the entire system of a medical apparatus according to a fourth embodiment of the invention.

As shown in FIG. 8A, as the driving shaft 57 is operated to be pulled toward the user side as shown by arrow A, the movable jaw 55 is moved to close toward the stationary jaw 54. In addition, as shown in FIG. 8B, as the driving shaft 57 is forced in the direction of the tip thereof as shown by arrow B, the movable jaw 55 is moved to open from the stationary jaw 54.

A thermal therapeutic unit 67 having approximately the same construction as the thermal therapeutic unit 14 of the therapeutic instrument 2 of the first embodiment is fitted to the stationary jaw 54. A plate-shaped receiving part 68 having approximately the same construction as the plate-shaped receiving part 36 of the therapeutic instrument 2 of the first embodiment is fitted to the movable jaw 55.

The proximal-end portion of the lead 25 connected to the thermal elements 23 (refer to FIGS. 2A and 2B) of the thermal therapeutic unit 67 are extended outwardly from the operating-section main body 63. A connector 69 is connected to the end of this extended portion of the lead 25.

The function of the above-described construction will be described below. During the use of the thermal coagulation incising forceps 51 according to the third embodiment, the user manipulates the stationary handle 64 and the movable handle 66 in the state of respectively inserting his/her finger and thumb through rings provided on the user sides of the stationary handle 64 and the movable handle 66, thereby turning the movable handle 66 with respect to the stationary handle 64 about the pivot shaft 65. In this manner, the driving shaft 57 is driven to move back and forth in the axial direction, and as the driving shaft 57 is moved back and forth, the movable jaw 55 is driven to rotate about the rotating shaft 58 with respect to the stationary jaw 54, whereby the stationary jaw 54 and the movable jaw 55 are operated to open and close.

Then, the user closes the movable jaw 55 and the stationary jaw 54 to clamp a living tissue between the movable jaw 55 and the stationary jaw 54, and energizes and heats the heat source part 15 (refer to FIGS. 2A and 2B) of the thermal therapeutic unit 67.

At this time, heat from the three thermal elements 23 of the heat source part 15 is conducted to the heat conducting plate 20 and the tapered blade edge part 21 of the heat conducting plate 20 is heated to a high temperature. Accordingly, the living tissue pressed in contact with the blade edge part 21 of the heat conducting plate 20 between the movable jaw 55 and the stationary jaw 54 is heated by the heat of the blade edge part 21, whereby the coagulation or the incision of the living tissue can be efficiently performed.

Accordingly, the third embodiment serves the following advantages. In the thermal therapeutic unit 67 of the thermal coagulation incising forceps 51 according to the third embodiment, the portion of the heat conducting plate 20 that extends upwardly from the blade edge part 21 and the thermal elements 23 are covered with the approximately U-shaped heat insulating frame 18. Consequently, heat generated in the heat source part 15 (the thermal elements 23) can be concentratedly and efficiently conducted to the heat conducting plate (therapeutic section) 20 which is higher in thermal conductivity than the heat insulating frame (holding section) 18, but can be prevented from being easily conducted to the jaws side. During the use of the thermal coagulation incising forceps 51, the heat of the thermal elements 23 can be prevented from dissipating in any direction other than the portion of contact between the thermal elements 23 and the heat conducting plate 20, for example, in rightward, leftward and upward directions from the heat conducting plate 20, whereby the heat of the thermal elements 23 such as the heat generating elements of the heat source part 15 can be concentratedly and efficiently conducted to the heat conducting plate 20 of the therapeutic part 16. Accordingly, the heat of the heat source part 15 can be prevented from being conducted to the stationary jaw 54. Accordingly, it is possible to prevent the degradation of the coagulation performance and the incision performance of the thermal coagulation incising forceps 51 due to the temperature of the heat conducting plate 20 in contact with a living tissue not increasing rapidly or a temperature nonuniformity occurring.

A fourth embodiment of the invention will be described below with reference to FIGS. 9 to 12. In the fourth embodiment, the construction of the therapeutic instrument 2 of the medical apparatus 1 according to the first embodiment (refer to FIGS. 1 to 4) is partly modified. Incidentally, the fourth embodiment is approximately the same as the first embodiment in the basic construction of the medical apparatus 1, and in the description of the fourth embodiment, the same reference numerals are used to denote the same sections, parts and portions as those of the first embodiment and the same description is omitted.

In the therapeutic instrument 2 of the fourth embodiment, the heat insulating frame 18 inside the first grasping section 7 uses a material, such as polytetrafluoroethylene (Teflon®), which is low in thermal conductivity and has high non-tackiness for preventing the sticking of a living tissue. The heat conducting plate 20 of the therapeutic part 16 uses a material, such as copper, which is high in thermal conductivity. A coating portion 71 such as Teflon® is formed on at least the edge portion of the blade edge part 21 of the heat conducting plate 20 so that non-tackiness is given to the external surface of the edge portion.

Figure 10A:
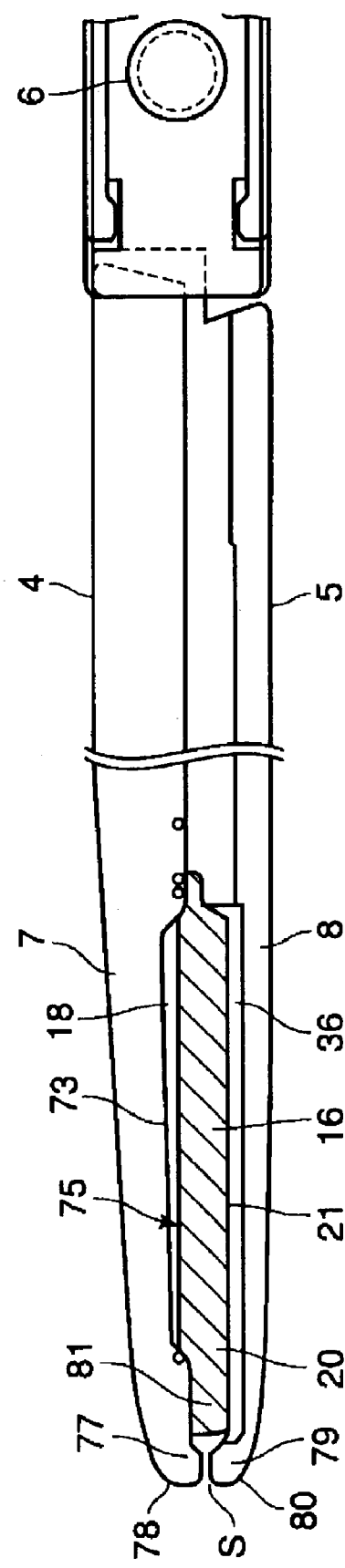
FIG. 10A is a side view showing a tip portion of a therapeutic instrument of the fourth embodiment.
Figure 10B:
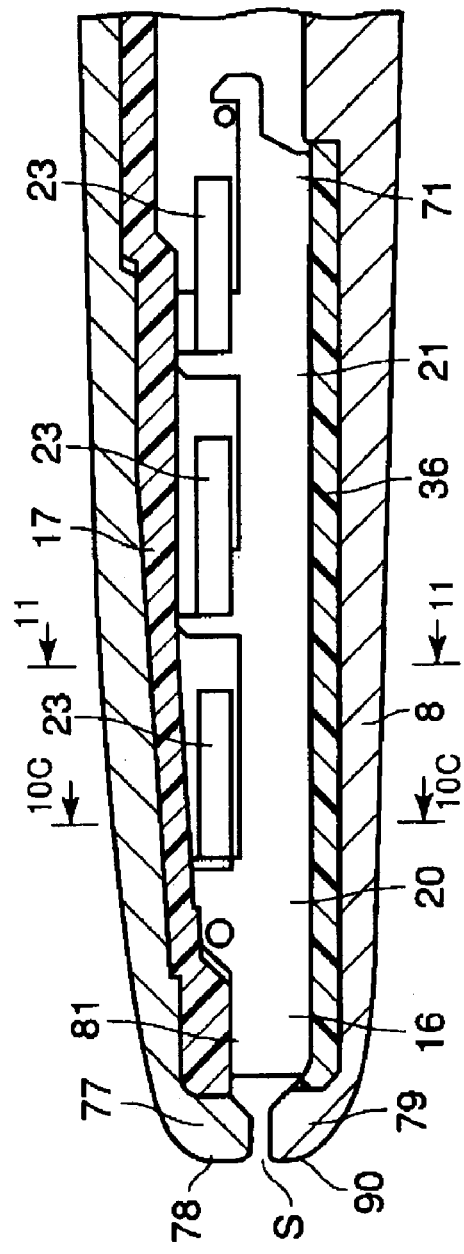
FIG. 10B is a longitudinal sectional view of the essential parts shown in FIG. 10A.
Figure 10C:
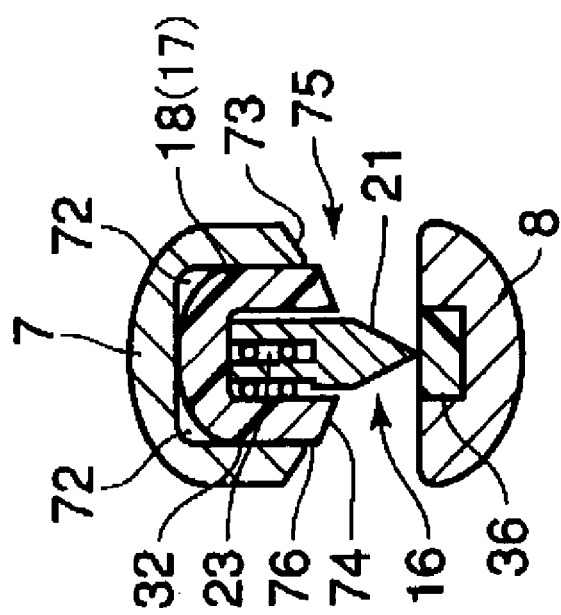
FIG. 10C is a cross-sectional view taken along line 10C—10C of FIG. 10A.

As shown in FIG. 10C, two grooves 72 (non-contact portion) for providing heat insulating air layers between the first grasping section 7 and the heat insulating frame 18 of the heat insulating part 17 are disposed to extend along the axial direction of the first grasping section 7 at the inside bottom of the concave fitting groove 32 of the first grasping section 7. Incidentally, the heat insulating frame 18 is constructed to indirectly hold the heating elements 23 via the heat conducting plate 20.

Figure 11:
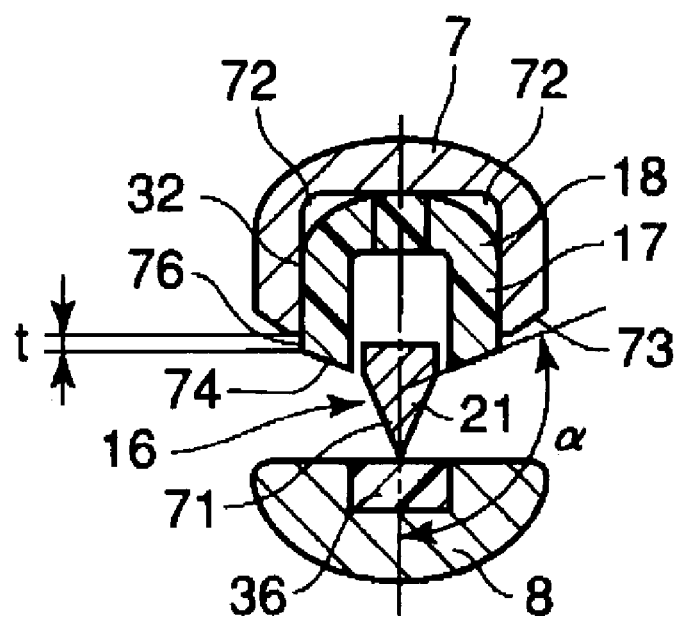
FIG. 11 is a cross-sectional view taken along line 11—11 of FIG. 10A.
Figure 12:
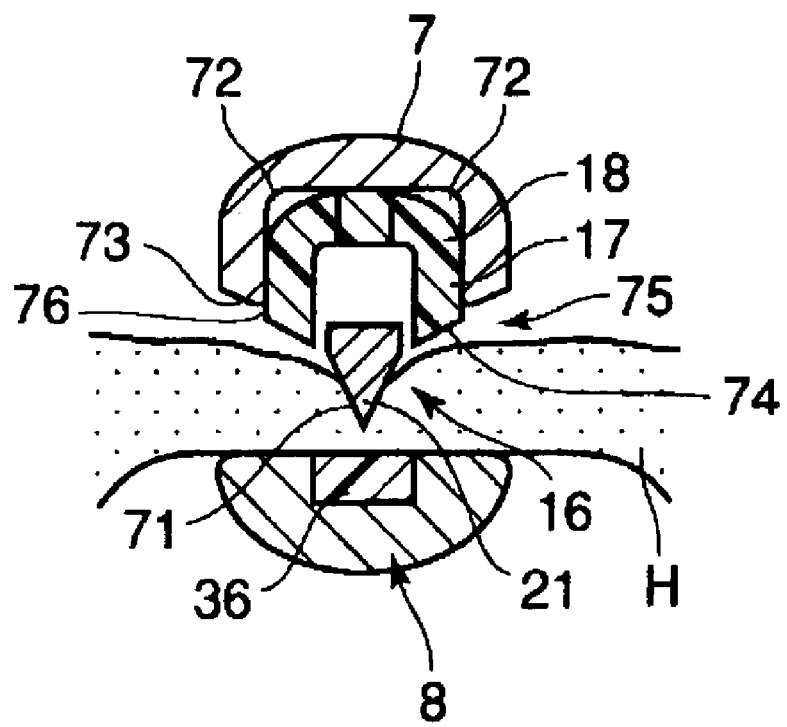
FIG. 12 is a longitudinal sectional view showing the state of use of the essential parts of the therapeutic instrument of the fourth embodiment.

As shown in FIG. 11, the opposite lateral sides of each of the first grasping section 7 and the heat insulating frame 18 have bottom surfaces which are respectively cut as surfaces 73 and 74 extending in obliquely upward directions. The angle a formed between each of the inclined surfaces 74 of the heat insulating frame 18 and the center line of the blade edge part 21 of the heat conducting plate 20 is set to be an angle (obtuse angle) of not smaller than 90°. Similarly, the angle α formed between each of the inclined surfaces 73 of the first grasping section 7 and the center line of the blade edge part 21 of the heat conducting plate 20 is set to be an angle (obtuse angle) of not smaller than 90°. Consequently, as shown in FIG. 12, the amount of exposure of the blade edge part 21 of the heat conducting plate 20 is increased, and a relief portion (contact preventing portion) 75 for preventing a living tissue from coming into contact with the opposite lateral side surfaces of the therapeutic part 16 when the living tissue is grasped between the blade edge part 21 of the first grasping section 7 and the second grasping section 8 is formed by each of the inclined surfaces 73 of the first grasping section 7 and the adjacent one of the inclined surfaces 74 of the heat insulating frame 18.

As shown in FIG. 11, the bottom ends of the heat insulating frame 18 are protruded downwardly from the bottom ends of the inclined surface 73 of the first grasping section 7. Accordingly, stepped portions 76 each having an appropriate length t are formed between the lower ends of the respective inclined surfaces 73 of the first grasping section 7 and the upper ends of the adjacent ones of the inclined surfaces 74 of the heat insulating frame 18. Consequently, as shown in FIG. 12, when a living tissue H is to be grasped between the blade edge part 21 of the first grasping section 7 and the second grasping section 8, the heat insulating frame 18 is brought into contact with the living tissue H before the living tissue H comes into abutment with the first grasping section 7, whereby the first grasping section 7 is prevented from coming into abutment with the living tissue H and allowing heat to dissipate. In addition, the living tissue H is prevented from sticking to the first grasping section 7.

In the fourth embodiment, as shown in FIGS. 10A and 10B, an extended portion 77 extended forwardly from the therapeutic part 16 is formed in the first grasping section 7. The extended portion 77 has a tapered portion 78 formed to become gradually thinner toward the tip of the extended portion 77. Similarly, the second grasping section 8 has an extended portion 79 having a shape corresponding to that of the extended portion 77 of the first grasping section 7. This extended portion 79 also has a tapered portion 80 formed to become gradually thinner toward the tip of the extended portion 79.

The first grasping section 7 and the second grasping section 8 are set so that when the first grasping section 7 and the second grasping section 8 are closed, a gap S is formed between the mutually opposed surfaces of the extended portion 77 of the first grasping section 7 and the extended portion 79 of the second grasping section 8. Accordingly, the first grasping section 7 and the second grasping section 8 have a structure which, when the first grasping section 7 and the second grasping section 8 are closed, allows the blade edge part 21 of the first grasping section 7 and the receiving part 36 of the second grasping section 8 to come into contact with each other, but does not allow the mutually opposed surfaces of the extended portion 77 of the first grasping section 7 and the extended portion 79 of the second grasping section 8 to come into contact with each other.

As shown in FIG. 10B, a forward extended portion 81 which are extended forwardly from the position where the heating elements 23 are secured is formed at the front end portion of the heat conducting plate 20. Accordingly, since heat of the heating elements 23 is conducted to the forward extended portion 81, the front end portion of the first grasping section 7 can be efficiently heated without the need to secure a special heating element 23 to the front end portion of the first grasping section 7. Consequently, the front end portion of the first grasping section 7 can be tapered as compared with the case in which such heating element 23 is secured to the first grasping section 7. Consequently, the user can perform manipulation such as dissection of the living tissue H by means of the extended portions 77 and 80 of the first grasping section 7 and the tapered portion 78 of the extended portion 79 of the second grasping section 8.

The function of the fourth embodiment will be described below. In the fourth embodiment, the user operates the first operating arm 4 and the second operating arm 5 of the therapeutic instrument 2 in the state of inserting his/her finger and thumb through the respective rings 9 provided on the user sides of the first operating arm 4 and the second operating arm 5, thereby turning the first operating arm 4 and the second operating arm 5 about the rotating shaft 6. In this manner, the first grasping section 7 and the second grasping section 8 are opened and closed. Then, as shown in FIG. 12, the user closes the first grasping section 7 and the second grasping section 8 to clamp the living tissue H between the first grasping section 7 and the second grasping section 8. At this time, the living tissue H is compressed between the tapered blade edge part 21 of the heat conducting plate 20 and the receiving part 36, and the living tissue H is grasped in a compressed state. Incidentally, the edge of the blade edge part 21 of the heat conducting plate 20 has an unsharp shape which is not so sharp as to cut the living tissue H, so that the living tissue H is prevented from being mechanically incised.

Subsequently, when the heating elements 23 are energized by the power source 3, each of the heating elements 23 of the heating therapeutic unit 14 is energized to generate heat. At this time, the heat of each of the heating elements 23 is conducted to the heat conducting plate 20, whereby the heat conducting plate 20 is heated. Owing to the heat, the portion of the living tissue H that is in contact with the heat conducting plate 20 and the receiving part 36 is coagulated in a high-pressure state.

Furthermore, the evaporation of moisture of the living tissue H proceeds with the coagulation of the living tissue H, so that the living tissue H which is embrittled is cut away to complete the dissection of the living tissue H.

Consequently, the fourth embodiment serves the following advantages. Namely, in the therapeutic instrument 2 of the fourth embodiment, the approximately U-like shaped heat insulating frame 18 covers the portion of the heat conducting plate 20 that extends upwardly from the blade edge part 21, and the thermal elements 23 (refer to FIG. 10C). Accordingly, heat generated in the heat source part 15 (the thermal elements 23) can be concentratedly and efficiently conducted to the heat conducting plate (therapeutic section) 20 which is higher in thermal conductivity than the heat insulating frame (holding section) 18, but can be prevented from being easily conducted to the jaws side. During the use of the medical apparatus 1, the heat of the thermal elements 23 can be prevented from dissipating in any direction other than the portion of contact between the thermal elements 23 and the heat contacting plate 20, for example, in rightward, leftward and upward directions from the heat contacting plate 20, whereby the heat of the thermal elements 23 such as the heat generating elements of the heat source part 15 can be concentratedly and efficiently conducted to the heat conducting plate 20 of the therapeutic part 16.

Consequently, even in the fourth embodiment, similarly to the case of the first embodiment, the heat of the heat source part 15 can be prevented from being conducted to the first grasping section 7. Accordingly, it is possible to prevent the degradation of the coagulation performance and the incision performance of the medical apparatus 1 due to the temperature of the heat conducting plate 20 in contact with a living tissue not increasing rapidly or a temperature nonuniformity occurring.

In addition, in the fourth embodiment, the opposite lateral sides of each of the metal-made, first grasping section 7 and the heat insulating frame 18 have the bottom surfaces which are respectively cut as the surfaces 73 and 74 extending in the obliquely upward directions, whereby the area of exposure of the blade edge part 21 of the heat conducting plate 20 is increased. Consequently, the area of contact between the blade edge part 21 of the heat conducting plate 20 and the living tissue H becomes wide to enable reliable coagulation.

Furthermore, the angle α formed between each of the inclined surfaces 74 of the heat insulating frame 18 and the center line of the blade edge part 21 of the heat conducting plate 20 is set to be an angle (obtuse angle) of not smaller than 90°. Similarly, the angle α formed between each of the inclined surfaces 73 of the first grasping section 7 and the center line of the blade edge part 21 of the heat conducting plate 20 is set to be an angle (obtuse angle) of not smaller than 90°. In addition, the relief portion 75 is formed. Consequently, when the blade edge part 21 of the first grasping section 7 and the second grasping section 8 are closed, the living tissue H can be prevented from coming into contact with the opposite side surfaces of the therapeutic part 16, owing to the relief portion 75 formed by each of the inclined surfaces 73 of the first grasping section 7 and the adjacent one of the inclined surfaces 74 of the heat insulating frame 18. Consequently, when the living tissue H is grasped between the blade edge part 21 of the first grasping section 7 and the second grasping section 8, pressure for pressing the living tissue H can be concentrated onto the blade edge part 21 of the first grasping section 7, whereby the blade edge part 21 of the first grasping section 7 can be brought into intimate contact with the living tissue H to fully compress the living tissue H. As a result, the living tissue H is coagulated with strong force, and further, the living tissue H can be incised by using heat at the same time as the coagulation of the living tissue H.

Since the heat insulating frame 18 is made of a non-tacky material and protrudes downwardly from the first grasping section 7, there is the advantage that the living tissue H does not stick to the first grasping section 7 and the heat insulating frame 18.

In addition, in the fourth embodiment, the bottom ends of the heat insulating frame 18 are protruded downwardly from the bottom ends of the inclined surfaces 73 of the first grasping section 7, and the stepped portions 76 each having an appropriate length t are formed between the lower ends of the respective inclined surfaces 73 of the first grasping section 7 and the upper ends of the adjacent ones of the inclined surfaces 74 of the heat insulating frame 18. Consequently, when the first grasping section 7 and the second grasping section 8 are closed, even if the living tissue H comes into abutment with the heat insulating frame 18, the portion of the living tissue H that comes into abutment with the heat insulating frame 18 is prevented from coming into contact with the bottom surfaces of the first grasping section 7.

In addition, since the respective tapered portions 78 and 80 which become gradually thinner toward the tip side are formed at the tip portions of the first grasping section 7 and the second grasping section 8, the respective tip portions of the first grasping section 7 and the second grasping section 8 can be made thin.

Furthermore, as shown in FIGS. 10A and 10B, the first grasping section 7 and the second grasping section 8 are set so that when the first grasping section 7 and the second grasping section 8 are closed, the gap S is formed between the mutually opposed surfaces of the extended portion 77 of the first grasping section 7 and the extended portion 79 of the second grasping section 8. Consequently, the first grasping section 7 and the second grasping section 8 have the structure which, when the first grasping section 7 and the second grasping section 8 are closed, allows the blade edge part 21 of the first grasping section 7 and the receiving part 36 of the second grasping section 8 to come into contact with each other, but does not allow the mutually opposed surfaces of the extended portion 77 of the first grasping section 7 and the extended portion 79 of the second grasping section 8 to come into contact with each other. Consequently, during coagulation and incision, compressive force can be concentrated onto the living tissue H grasped between the blade edge part 21 of the heat conducting plate 20 and the receiving part 36.

Furthermore, the heat conducting plate 20 is made of a material which is high in thermal conductivity, and the heat of the heating elements 23 can be conducted to the forward extended portion 81 which is extended forwardly from the position where the heating elements 23 are secured. Accordingly, the front end portion of the first grasping section 7 can be efficiently heated without the need to secure the special heating element 23 to the front end portion of the first grasping section 7. Consequently, the front end portion of the first grasping section 7 can be reduced in height to be tapered, as compared with the case in which such heating element 23 is secured to the first grasping section 7. Consequently, the user can perform manipulation such as dissection of the living tissue H by means of the extended portion 77 of the first grasping section 7 and the tapered portions 78 and 80 of the extended portion 79 of the extended portion 79.

Figure 10D:
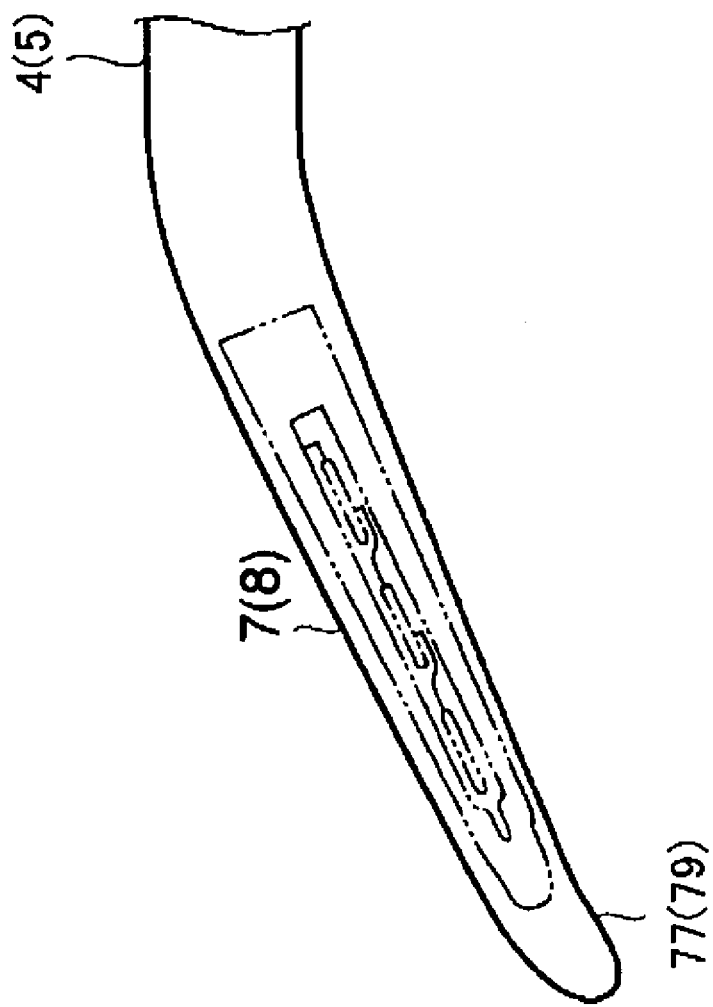
FIG. 10D is a plan view of a grasping section according to a modified forth embodiment of the invention.

FIG. 10D is a plan view of the grasping section according to a modification of the forth embodiment. In this modified embodiment, the extending direction of the first grasping section 7 and that of the second grasping section 8 are different from that of the first manipulation arm 4 and that of the second manipulation arm 5. In this modified embodiment, the angle between the extending direction of the first manipulation arm 4 and that of the first grasping section 7 (the angle between the extending direction of the second manipulation arm 5 and that of the second grasping section 8) is more than 0 degree and smaller than 90 degree. Furthermore, the extending direction of the first grasping section 7 and that of the second grasping section are different from that of the extended portion 77 of the first grasping section 7 and that of the extended portion 79 of the second grasping section 8. In this modified embodiment, the angle between the extending direction of the first grasping section 7 and the extended portion 77 (the angle between the second grasping section 8 and the extended portion 79) is more than 0 degree and less smaller than 90 degree.

As shown, by having different extending directions between the grasping sections (jaws) and the operating arms, an ablation of the living tissue becomes easy. Furthermore, by having different extending directions between the grasping sections (jaws) and their extended portions, an ablation of the living tissue also becomes easy.

A fifth embodiment of the invention will be described with reference to FIGS. 13A, 13B, 14A and 14B. FIG. 13A shows a therapeutic instrument 91 according to the fifth embodiment. This therapeutic instrument 91 includes an elongated inserting section 92 and a user-side operating section 93 that is connected to the proximal side of this inserting section 92. The tip of the inserting section 92 has a pair of grasping sections (jaws) 94 and 95 (the first grasping section 94 and the second grasping section 95).

The user-side operating section 93 has a operating-section main body 96, a handle 97 provided integrally with the operating-section main body 96, and a movable handle 99 provided on the operating-section main body 96 for turning movement about a pivot shaft 98. In addition, the operating-section main body 96 has a rotary operating section 100 for operating the inserting section 92 so that the inserting section 92 is rotated about the central axis of the inserting section 92 in an axial rotational direction.

As shown in FIG. 13B, the inserting section 92 includes an outer pipe 101 formed of a thin pipe. A channel pipe 102 and a driving-shaft channel 103 are provided to extend in parallel with each other in the interior of the outer pipe 101. An inserting space 104 through which a coaxial cable 127 which will be described later is inserted is provided in the interior of the channel pipe 102. A driving shaft 105 is inserted through the driving-shaft channel 103 for movement back and forth therein. The proximal end of the driving shaft 105 is connected to a movable handle 99. The driving shaft 105 is driven to move back and forth in the axial direction in interlocking relationship to the turning movement of the movable handle 99.

A forked supporting member 106 that is forwardly protruded is provided in the distal tip portion of the inserting section 92. A root portion 106*a* of this supporting member 106 is fixed to the distal tip of the outer pipe 101. A pivot pin 107 is provided to extend laterally through the opposite distal tip portions of the supporting member 106. The proximal end of the second grasping section 95 is turnably supported by the pivot pin 107.

A forked portion 94*a* is formed in the proximal end portion of the first grasping section 94. This forked portion 94*a* is turnably connected to the driving shaft 105 via a connecting pin 108. In addition, a forked connecting portion 95*a* is formed in the proximal end portion of the second grasping section 95. This connecting portion 95*a* is turnably connected to the forked portion 94*a* of the first grasping section 94 by a connecting pin 109.

Accordingly, as shown in FIG. 13A, as the movable handle 99 is turned in the direction of arrow a, the driving shaft 105 advances. During the advance of the driving shaft 105, the first grasping section 94 turns upwardly about the connecting pin 109, while the second grasping section 95 turns downwardly about the pivot pin 107, so that the first grasping section 94 and the second grasping section 95 are opened. Contrarily, as the movable handle 99 is turned in the direction of arrow b, the driving shaft 105 withdraws. During the withdrawal of the driving shaft 105, the first grasping section 94 turns downwardly about the connecting pin 109, while the second grasping section 95 turns upwardly about the pivot pin 107, so that the first grasping section 94 and the second grasping section 95 are closed.

The structures of the first grasping section 94 and the second grasping section 95 are similar to the structures of the first grasping section 7 and the second grasping section 8 of the fourth embodiment (refer to FIGS. 9 to 12). Namely, as shown in FIG. 14B, a heating therapeutic unit 110 having approximately the same construction as the heating therapeutic unit 14 of the therapeutic instrument 2 according to the first embodiment is fitted in the interior of the first grasping section 94. The heat insulating part 110 includes a heat insulating frame 111 having an approximately U-like cross-sectional shape. The top portion of a heat conducting plate 112 is fixed to the heat insulating frame 111. Heating elements 113 are fixed to the top portion of the heat conducting plate 112. By means of the heat insulating frame 111, the heat of the heating elements 113 is prevented from being radiated toward the first grasping section 94. Incidentally, the heat insulating frame 111 is constructed to indirectly hold the heating elements 113 via the heat conducting plate 112.

Two grooves 114 for providing heat insulating air layers are disposed to extend along the axial direction of the first grasping section 94 at the inside bottom of the first grasping section 94. A coating portion 116 such as Teflon® is formed on at least the edge portion of the blade edge part 115 of the heat conducting plate 112 so that non-tackiness is given to the external surface of the edge portion. Incidentally, the number of the grooves 114 is not limited to two, and the grooves 114 may also include one or three or more grooves constructed to achieve the purpose of insulating or reducing heat to be conducted from the heat insulating frame 111 to the first grasping section 94.

A plate-shaped receiving part 117 made of a flexible material which does not easily conduct heat, such as fluororesin or silicone, is provided on the surface of the second grasping section 95 that is opposite to the first grasping section 94. Accordingly, when the user closes the first grasping section 94 and the second grasping section 95, the whole of the blade edge part 115 of the heat conducting plate 112 is received by the receiving part 117 in the state of being in contact with the receiving part 117. Then, the user clamps a living tissue between the first grasping section 94 and the second grasping section 95 with the first and second grasping sections 94 and 95 closed, and performs incision or coagulation on the living tissue.

The opposite lateral sides of each of the first grasping section 94 and the heat insulating frame 111 have bottom surfaces which are respectively cut as surfaces 118 and 119 extending in obliquely upward directions. The angle α formed between each of the inclined surfaces 119 of the heat insulating frame 111 and the center line of the blade edge part 115 of the heat conducting plate 112 is set to be an angle (obtuse angle) of not smaller than 90°. Similarly, the angle α formed between each of the inclined surfaces 118 of the first grasping section 94 and the center line of the blade edge part 115 of the heat conducting plate 112 is set to be an angle (obtuse angle) of not smaller than 90°. Accordingly, the amount of exposure of the blade edge part 115 of the heat conducting plate 112 is increased. A relief portion (contact preventing portion) 120 for preventing a living tissue from coming into contact with the opposite lateral side surfaces of the therapeutic part when the living tissue is grasped between the blade edge part 115 of the first grasping section 94 and the second grasping section 95 is formed. The relief portion is formed by each of the inclined surfaces 118 of the first grasping section 94 and the adjacent one of the inclined surfaces 119 of the heat insulating frame 111.

Furthermore, the position of the distal tip of the heat insulating frame 111 which covers the top portion of the heat conducting plate 112 is set to extend to a position protruding forwardly from the position of the distal tip of the heat conducting plate 112. Similarly, the position of the rear end of the heat insulating frame 111 extends further rearwardly from the position of the rear end of the heat conducting plate 112 and covers the rear end of the heat conducting plate 112.

The bottom ends of the heat insulating frame 111 are protruded downwardly from the bottom ends of the inclined surface 117 of the first grasping section 94. Accordingly, stepped portions 121 each having an appropriate length t are formed between the lower ends of the respective inclined surfaces 118 of the first grasping section 94 and the upper ends of the adjacent ones of the inclined surfaces 119 of the heat insulating frame 111. Consequently, when the living tissue H is to be grasped between the blade edge part 115 of the first grasping section 94 and the second grasping section 95, the heat insulating frame 111 is brought into contact with the living tissue H before the living tissue H comes into abutment with the first grasping section 94, whereby the first grasping section 94 is prevented from coming into abutment with the living tissue H and allowing heat to escape.

In addition, in the fifth embodiment, an extended portion 122 extended forwardly from the therapeutic part 94 is formed in the first grasping section 94. The extended portion 122 has a tapered portion 123 formed to become gradually thinner toward the tip of the extended portion 122. Similarly, the second grasping section 95 has an extended portion 124 having a shape corresponding to that of the extended portion 122 of the first grasping section 94. This extended portion 124 also has a tapered portion 125 formed to become gradually thinner toward the tip of the extended portion 124.

Furthermore, as shown in FIG. 14A, the first grasping section 94 and the second grasping section 95 are set so that when the first grasping section 94 and the second grasping section 95 are closed, the gap S is formed between the mutually opposed surfaces of the extended portion 122 of the first grasping section 94 and the extended portion 124 of the second grasping section 95.

The operating-section main body 96 also has a connector connecting portion 126. A connecting portion 12 (refer to FIG. 1) provided at one end of the cable 11 (refer to FIG. 1) extending from the power source 3 (refer to FIG. 1) is removably connected to the connector connecting portion 126 similarly to the case of the first embodiment. The coaxial cable 127 which is inserted through the interior of the channel pipe 102 is connected at one end to the connector connecting portion 126. The other end of the coaxial cable 127 is connected to the heating elements 113 of the heating therapeutic unit 110 of the first grasping section 94.

The function of the fifth embodiment having the above-described construction will be described below. In the case of the therapeutic instrument 91 of the fifth embodiment, when the movable handle 99 of the user-side operating section 93 is operated, the first grasping section 94 and the second grasping section 95 are opened and closed to grasp a living tissue. Then, when the heating elements 113 of the heating therapeutic unit 110 are energized with the living tissue grasped between the first grasping section 94 and the second grasping section 95, each of the heating elements 113 of the heating therapeutic unit 110 is energized to generate heat. Consequently, the living tissue pressed in contact with the blade edge part 115 of the heat conducting plate 112 between the first grasping section 94 and the second grasping section 95 is heated by the heat of the blade edge part 115, whereby the coagulation or the incision of the living tissue can be efficiently performed.

Consequently, the fifth embodiment serves the following advantages. In the therapeutic unit 91 according to the fifth embodiment, the portion of the heat conducting plate 112 that extends upwardly from the blade edge part 115 and the thermal elements 113 are covered with the approximately U-shaped heat insulating frame 111. Accordingly, heat generated in the thermal elements (heat source part) 113 can be concentratedly and efficiently conducted to the heat conducting plate (therapeutic section) 112 which is higher in thermal conductivity than the heat insulating frame (holding section) 111, but can be prevented from being easily conducted to the jaws side. During the use of the medical apparatus, the heat of the thermal elements 113 can be prevented from dissipating in any direction other than the portion of contact between the thermal elements 113 and the heat conducting plate 112, for example, in rightward, leftward and upward directions from the heat conducting plate 112, whereby the heat of the thermal elements 113 such as the heat generating elements of the heat source part can be concentratedly and efficiently conducted to the heat conducting plate 112. Consequently, even in the fifth embodiment, similarly to the case of the first embodiment, the heat of the heat conducting plate 112 can be prevented from being conducted to the first grasping section 94. Consequently, it is possible to prevent the degradation of the coagulation performance and the incision performance of the medical apparatus 1 due to the temperature of the heat conducting plate 112 in contact with a living tissue not increasing rapidly or a temperature nonuniformity occurring. Accordingly, since the living tissue is fully compressed between the blade edge part 115 of the heat conducting plate 112 and the receiving part 117 of the second grasping section 95, reliable coagulation and incision can be performed and treatment can be performed as desired by the user.

In the fifth embodiment, the opposite lateral sides of each of the metal-made, first grasping section 94 and the heat insulating frame 111 have the bottom surfaces which are respectively cut as the surfaces 118 and 119 extending in the obliquely upward directions, whereby the area of exposure of the blade edge part 115 of the heat conducting plate 112 is increased. Accordingly, the area of contact between the blade edge part 115 of the heat conducting plate 112 and the living tissue H becomes wide to enable reliable coagulation. Accordingly, even if the height of the first grasping section 94 is not increased, the area of an exposed portion of the blade edge part 115 of the heat conducting plate 112 can be ensured to such an extent that satisfactory coagulation performance can be obtained.

Furthermore, the angle α formed between each of the inclined surfaces 118 of the heat insulating frame 111 and the center line of the blade edge part 115 of the heat conducting plate 112 is set to be an angle (obtuse angle) of not smaller than 90°. Similarly, the angle α formed between each of the inclined surfaces 118 of the first grasping section 94 and the center line of the blade edge part 115 of the heat conducting plate 112 is set to be an angle (obtuse angle) of not smaller than 90°. In addition, the relief portion 120 is formed. Consequently, when the blade edge part 115 of the first grasping section 94 and the second grasping section 95 are closed, the living tissue H can be prevented from coming into contact with the opposite side surfaces of the therapeutic part, owing to the relief portion 120 formed by each of the inclined surfaces 118 of the first grasping section 94 and the adjacent one of the inclined surfaces 119 of the heat insulating frame 111.

Consequently, when the living tissue H is grasped between the blade edge part 115 of the first grasping section 94 and the second grasping section 95, pressure for pressing the living tissue H can be concentrated onto the blade edge part 115 of the first grasping section 94, whereby the blade edge part 115 of the first grasping section 94 can be brought into intimate contact with the living tissue H to fully compress the living tissue H. As the result, the living tissue H is coagulated with strong force, and further, the living tissue H can be incised by using heat at the same as the coagulation of the living tissue H.

Since the heat insulating frame 111 is made of a non-tacky material and protrudes downwardly from the first grasping section 94, there is the advantage that the living tissue H does not stick to the first grasping section 94 and the heat insulating frame 111.

In addition, in the fifth embodiment, the bottom ends of the heat insulating frame 111 are protruded downwardly from the bottom ends of the first grasping section 94, and the stepped portions 121 each having the appropriate length t are formed between the lower ends of the respective first grasping section 94 and the upper ends of the adjacent ones of the inclined surfaces 119 of the heat insulating frame 111.

Consequently, when the first grasping section 94 and the second grasping section 95 are closed, even if the living tissue H comes into abutment with the heat insulating frame 111, the portion of the living tissue H that comes into abutment with the heat insulating frame 111 is prevented from coming into contact with the bottom surfaces of the first grasping section 94.

In addition, since the respective tapered portions 122 and 124 which become gradually thinner toward the distal tip side are formed at the distal tip portions of the first grasping section 94 and the second grasping section 95, the respective distal tip portions of the first grasping section 94 and the second grasping section 95 can be made thin.

Furthermore, the first grasping section 94 and the second grasping section 95 are set so that when the first grasping section 94 and the second grasping section 95 are closed, the gap S is formed between the mutually opposed surfaces of the extended portion 122 of the first grasping section 94 and the extended portion 124 of the second grasping section 95. Accordingly, the first grasping section 94 and the second grasping section 95 have the structure which, when the first grasping section 94 and the second grasping section 95 are closed, allows the blade edge part 115 of the first grasping section 94 and the receiving part 117 of the second grasping section 95 to come into contact with each other, but does not allow the mutually opposed surfaces of the extended portion 122 of the first grasping section 94 and the extended portion 124 of the second grasping section 95 to come into contact with each other. Accordingly, during coagulation and incision, compressive force can be concentrated onto the living tissue H grasped between the blade edge part 115 of the heat conducting plate 112 and the receiving part 117.

Furthermore, the heat conducting plate 112 is made of a material which is high in thermal conductivity, and the heat of the heating elements 113 can be conducted to the forward extended portion of the heat conducting plate 112 that is extended forwardly from the position where the heating elements 113 are secured. Consequently, the front end portion of the first grasping section 94 can be efficiently heated without the need to secure the special heating element 113 to the front end portion of the first grasping section 94. Consequently, the front end portion of the first grasping section 94 can be reduced in height to be tapered, as compared with the case in which such heating element 113 is secured to the front end portion of the first grasping section 94. Consequently, the user can perform manipulation such as dissection of the living tissue H by means of the extended portion 122 of the first grasping section 94 and the tapered portions 123 and 125 of the extended portion 124 of the extended portion 95.

A sixth embodiment of the invention will be described with reference to FIGS. 15A and 15B. In the sixth embodiment, the internal construction of the first grasping section 7 in the therapeutic instrument 2 according to the first embodiment (refer to FIGS. 1 to 4) is modified in part.

Figure 15A:
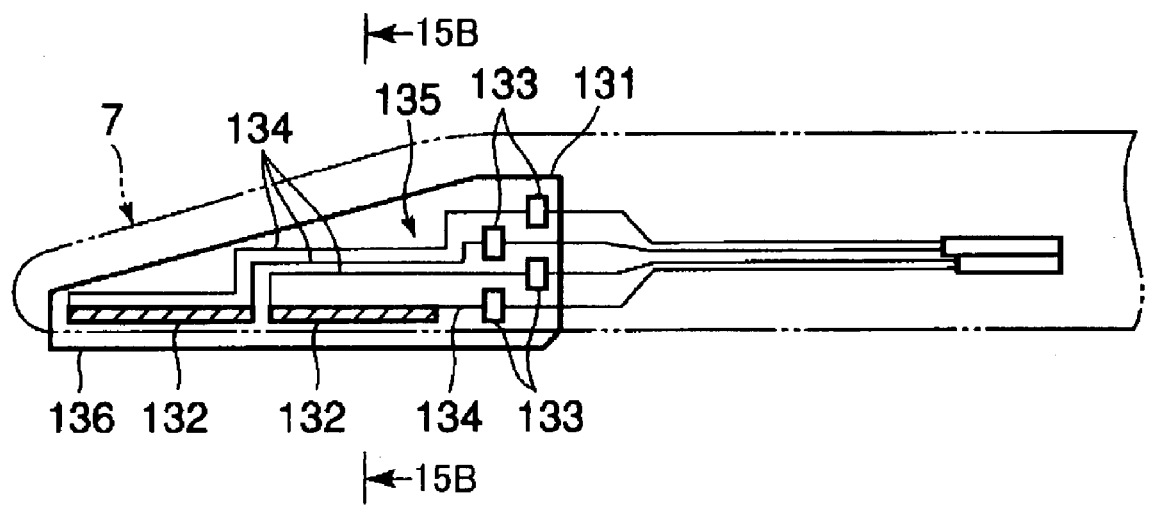
FIG. 15A is a schematic construction view of the interior of a jaw of a therapeutic instrument according to a sixth embodiment.

Namely, as shown in FIG. 15A, in the sixth embodiment, the therapeutic part 16 inside the first grasping section 7 is formed as one element 135 which includes in integrated form heating elements 132 formed by thin film resistance semiconductors on a surface of a plate-shaped base 131 having an approximately triangular shape which becomes gradually smaller in height, electrodes 133 for receiving current from the outside, and lead portions 134 connecting the heating elements 132 and the electrodes 133, and the like.

A plate which constitutes the base 131 of this element 135 is formed of a material which can easily conduct heat, such as copper, copper alloy, aluminum alloy, tungsten or molybdenum. The whole of the element 135 is heated by heat generated at the heating elements 132.

Figure 15B:
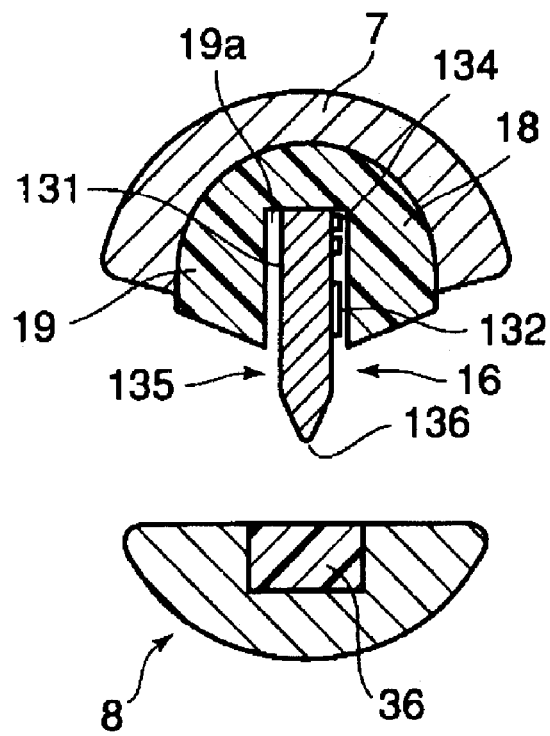
FIG. 15B is a cross-sectional view taken along line 15B—15B of FIG. 15A.

As shown in FIG. 15B, a bottom edge portion 136 of the element 135 has a tapered cross-sectional shape. The top flat portion (as viewed in FIG. 15B) of the element 135 is accommodated in the groove-shaped accommodating space 19a inside the holding frame 19 of the heat insulating frame 18, and is fixed in the state of being surrounded by being covered by the heat insulating frame 18 which is the holding frame 19. Furthermore, the tapered portion of the bottom edge portion 136 of the element 135 is held in the state of being exposed from the holding frame 19, whereby the bottom edge portion 136 can be brought into contact with a living tissue. Incidentally, the entire outer surfaces of the element 135 except the electrodes 133 are covered with a thin coat such as Teflon® so that a living tissue or blood is prevented from sticking to the element 135.

The function of the sixth embodiment will be described below. During the use of the therapeutic instrument 2 of the sixth embodiment, when the heating elements 132 on the element 135 generate heat, the entire element 135 is heated. Then, when the user closes the first and second grasping sections 7 and 8 to clamp the living tissue H between the first grasping section 7 and the second grasping section 8, the bottom edge portion 136 of the element 135 of the first grasping section 7 is brought into contact with the living tissue H, whereby the user can perform thermal coagulation, incision and the like on the living tissue H.

The sixth embodiment has the following advantages. Namely, in the sixth embodiment, it is possible to realize a series of functions which cause the single element 135 having the heating elements 132 and the bottom edge portion 136 to allow electric current to flow, generate heat and treat the living tissue H. Consequently, since the number of constituent parts of the therapeutic part 16 inside the first grasping section 7 is reduced, the medical apparatus becomes easy in assembly and stable in quality, and the cost thereof can be reduced. In addition, since the number of constituent parts of the therapeutic part 16 inside the first grasping section 7 is reduced, there is also the advantage that the frequency with which failures occur can be lowered.

According to the invention, it is possible to provide a medical apparatus which can highly efficiently conduct heat generated at a heat source part to a therapeutic section and can also provide good coagulation performance and incision performance and is excellent in durability.

Incidentally, the grasping sections of the invention are not necessarily formed as a jaws part (in which two grasping sections are opened and closed about one turning shaft). For example, the invention is applicable to a mechanism which opens and closes two grasping sections by means of parallel displacement like a vice, and a mechanism which grasps a living tissue by clamping in a closed loop (shrinks the closed loop to fix a living tissue and then expands the closed loop to release the living tissue).

In addition, although a blade edge part may be formed in the bottom portion of a heat conducting plate, a blade edge part and a heat conducting plate may also be separately prepared so that the blade edge part and the heat conducting plate are assembled in contact with each other.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical apparatus comprising:
a grasping section for grasping a living tissue;
a therapeutic part having a blade for applying thermal treatment to the living tissue, the blade being provided in the grasping section on a side thereof which contacts the living tissue; and
a heat insulating part made of a material lower in thermal conductivity than the blade, the heat insulating part being disposed between the grasping section and the blade;
wherein the heat insulating part holds at least the blade and a space between the heat insulating part and the blade is filled with a filler having heat insulating properties.

2. A medical apparatus comprising:
a grasping section for grasping a living tissue;
a therapeutic part having a blade for applying thermal treatment to the living tissue, the blade being provided in the grasping section on a side thereof which contacts the living tissue; and
a heat insulating part made of a material lower in thermal conductivity than the blade, the heat insulating part being disposed between the grasping section and the blade;
wherein the blade is movably fixed to the grasping section with a predetermined margin for a variation due to heat in at least one of a size or length of the blade.

3. A medical apparatus according to claim 2, wherein the fixation of the blade is realized by a pin being fitted into a hole formed in the grasping section to receive the pin with a predetermined margin.

4. A medical apparatus according to claim 3, wherein the hole is an elongated slot which is elongated in approximately a same direction as a longitudinal direction of the therapeutic part.

5. A medical apparatus
a grasping section for grasping a living tissue;
a therapeutic part having a blade for applying thermal treatment to the living tissue, the blade being provided in the grasping section on a side thereof which contacts the living tissue; and
a heat insulating part made of a material lower in thermal conductivity than the blade, the heat insulating part being disposed between the grasping section and the blade;
wherein the grasping section has a pair of jaws that are relatively movable between opened and closed positions and each of the pair of jaws have an extended portions extended forwardly from the blade and each of the extended portions has a tapered portion.

6. A medical apparatus
a grasping section for grasping a living tissue;
a therapeutic part having a blade for applying thermal treatment to the living tissue, the blade being provided in the grasping section on a side thereof which contacts the living tissue; and
a heat insulating part made of a material lower in thermal conductivity than the blade, the heat insulating part being disposed between the grasping section and the blade;
wherein the grasping section has a pair of jaws that are relatively movable between opened and closed positions and the pair of jaws respectively have extended portions extended forwardly, the extended portion extending in a direction other than a direction of the jaws.

7. A medical apparatus
a grasping section for grasping a living tissue;
a therapeutic part having a blade for applying thermal treatment to the living tissue, the blade being provided in the grasping section on a side thereof which contacts the living tissue; and
a heat insulating part made of a material lower in thermal conductivity than the blade, the heat insulating part being disposed between the grasping section and the blade;
wherein the grasping section has a pair of laws that are relatively movable between opened and closed positions and the pair of jaws respectively have extended portions extended forwardly such that, a gap occurs between the extended portions of the pair of jaws when the pair of jaws are in the closed position.

* * * * *